United States Patent
Kobayashi et al.

(10) Patent No.: US 11,931,202 B2
(45) Date of Patent: Mar. 19, 2024

(54) ULTRASOUND AUTOMATIC SCANNING SYSTEM, ULTRASOUND DIAGNOSTIC APPARATUS, ULTRASOUND SCANNING SUPPORT APPARATUS

(71) Applicant: CANON MEDICAL SYSTEMS CORPORATION, Otawara (JP)

(72) Inventors: Yusuke Kobayashi, Nasushiobara (JP); Satoshi Matsunaga, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 823 days.

(21) Appl. No.: 16/559,213

(22) Filed: Sep. 3, 2019

(65) Prior Publication Data
US 2020/0069284 A1 Mar. 5, 2020

(30) Foreign Application Priority Data

Sep. 3, 2018 (JP) .................................. 2018-164384
Sep. 2, 2019 (JP) .................................. 2019-159443

(51) Int. Cl.
*A61B 8/00* (2006.01)

(52) U.S. Cl.
CPC .............. *A61B 8/4209* (2013.01); *A61B 8/40* (2013.01); *A61B 8/4245* (2013.01);
(Continued)

(58) Field of Classification Search
None
See application file for complete search history.

(56) References Cited

U.S. PATENT DOCUMENTS 4,759,375 A 7/1988 Namekawa
5,335,547 A 8/1994 Nakajima et al.
(Continued)

FOREIGN PATENT DOCUMENTS

JP 62-152437 A 7/1987
JP 3-123857 A 5/1991
(Continued)

OTHER PUBLICATIONS

Japanese Office Action dated Feb. 14, 2023, in Japanese Patent Application No. 2019-159443, 4 pages.

*Primary Examiner* — Katherine L Fernandez
(74) *Attorney, Agent, or Firm* — Oblon, McClelland, Maier & Neustadt, L.L.P.

(57) ABSTRACT

An ultrasound automatic scanning system according to an embodiment includes an ultrasound probe, a mechanical mechanism, and processing circuitry. The ultrasound probe transmits and receives ultrasonic wave. The mechanical mechanism holds and moves the ultrasound probe while an ultrasonic-wave transmission-reception surface of the ultrasound probe is pointed to a subject. The processing circuitry acquires a distance between a body surface of the subject and the ultrasonic-wave transmission-reception surface of the ultrasound probe based on reflected wave data collected while the ultrasound probe is moved by the mechanical mechanism. The processing circuitry generates, based on information of the distance, locus information of movement of the ultrasound probe when ultrasound scanning is executed on the subject. The mechanical mechanism executes ultrasound scanning on the subject by moving the ultrasound probe based on the locus information generated by the processing circuitry.

15 Claims, 15 Drawing Sheets

(52) U.S. Cl.
CPC ............ *A61B 8/4281* (2013.01); *A61B 8/429* (2013.01); *A61B 8/467* (2013.01)

(56) References Cited

U.S. PATENT DOCUMENTS

| | | | | |
|---|---|---|---|---|
| 2003/0216648 | A1* | 11/2003 | Lizzi | A61B 8/0858 601/2 |
| 2005/0228254 | A1* | 10/2005 | Torp | A61B 8/08 600/407 |
| 2010/0099988 | A1* | 4/2010 | Kurita | G01S 7/52084 600/443 |
| 2011/0000299 | A1* | 1/2011 | Isobe | G01N 29/265 73/625 |
| 2014/0221825 | A1* | 8/2014 | Mahfouz | A61B 8/5223 600/443 |
| 2015/0057545 | A1* | 2/2015 | Takagi | G06T 7/0012 600/443 |
| 2016/0100821 | A1* | 4/2016 | Eggers | A61B 8/54 600/424 |
| 2016/0242738 | A1 | 8/2016 | Kiyan et al. | |
| 2017/0143303 | A1* | 5/2017 | Chen | A61B 8/488 |
| 2017/0347991 | A1* | 12/2017 | Mahfouz | A61B 8/483 |

FOREIGN PATENT DOCUMENTS

| | | |
|---|---|---|
| JP | 2004-337312 A | 12/2004 |
| JP | 2005-106654 A | 4/2005 |
| JP | 2007-185212 A | 7/2007 |
| JP | 2009-225904 A | 10/2009 |
| JP | 2012-235850 A | 12/2012 |
| WO | WO2015/053008 A1 | 4/2015 |

\* cited by examiner

ULTRASOUND AUTOMATIC SCANNING SYSTEM, ULTRASOUND DIAGNOSTIC APPARATUS, ULTRASOUND SCANNING SUPPORT APPARATUS

CROSS-REFERENCE TO RELATED APPLICATIONS

This application is based upon and claims the benefit of priority from Japanese Patent Application No. 2018-164834, filed on Sep. 3, 2018 and Japanese Patent Application No. 2019-159443, filed on Sep. 2, 2019; the entire contents of which are incorporated herein by reference.

FIELD

Embodiments discussed herein relate generally to an ultrasound automatic scanning system, an ultrasound diagnostic apparatus, and an ultrasound scanning support apparatus.

BACKGROUND

In conventionally performed ultrasound diagnosis, an engineer or a doctor operates an ultrasound probe on the body surface of a subject to obtain information of a tissue structure, blood current, and the like inside the body. For example, the engineer or the doctor scans the inside of the subject with ultrasonic wave by operating, on the body surface in accordance with a diagnosis site and a diagnosis content, the ultrasound probe configured to transmit and receive ultrasonic wave, thereby collecting an ultrasonic wave image illustrating a tissue structure and an ultrasonic wave image illustrating information of blood current or the like.

Recently, scanning by a robot in such ultrasonic wave diagnosis has been disclosed. For example, in a known technology, position information of the body surface of a subject is acquired from a picture obtained by capturing the subject with a camera, a scanning path indicating the movement locus of an ultrasound probe is generated from the acquired position information, and the ultrasound probe is moved along the generated scanning path by the robot.

DETAILED DESCRIPTION

An ultrasound automatic scanning system includes an ultrasound probe, a mechanical mechanism, and processing circuitry. The ultrasound probe is configured to transmit and receive ultrasonic wave. The mechanical mechanism is configured to hold and move the ultrasound probe while an ultrasonic-wave transmission-reception surface of the ultrasound probe is pointed to a subject. The processing circuitry is configured to acquire a distance between a body surface of the subject and the ultrasonic-wave transmission-reception surface of the ultrasound probe based on reflected wave data collected while the ultrasound probe is moved by the mechanical mechanism. The processing circuitry is configured to generate, based on information of the distance, locus information of movement of the ultrasound probe when ultrasound scanning is executed on the subject. The mechanical mechanism is configured to execute ultrasound scanning on the subject by moving the ultrasound probe based on the locus information generated by the processing circuitry.

Embodiments of an ultrasound automatic scanning system, an ultrasound diagnostic apparatus, and an ultrasound scanning support apparatus according to the present application will be described in detail below with reference to the accompanying drawings. The ultrasound automatic scanning system, the ultrasound diagnostic apparatus, and the ultrasound scanning support apparatus according to the present application are not limited to the embodiments described below. In the following description, identical components are denoted by a common reference sign, and duplicate description thereof will be omitted.

First Embodiment

Figure 1:
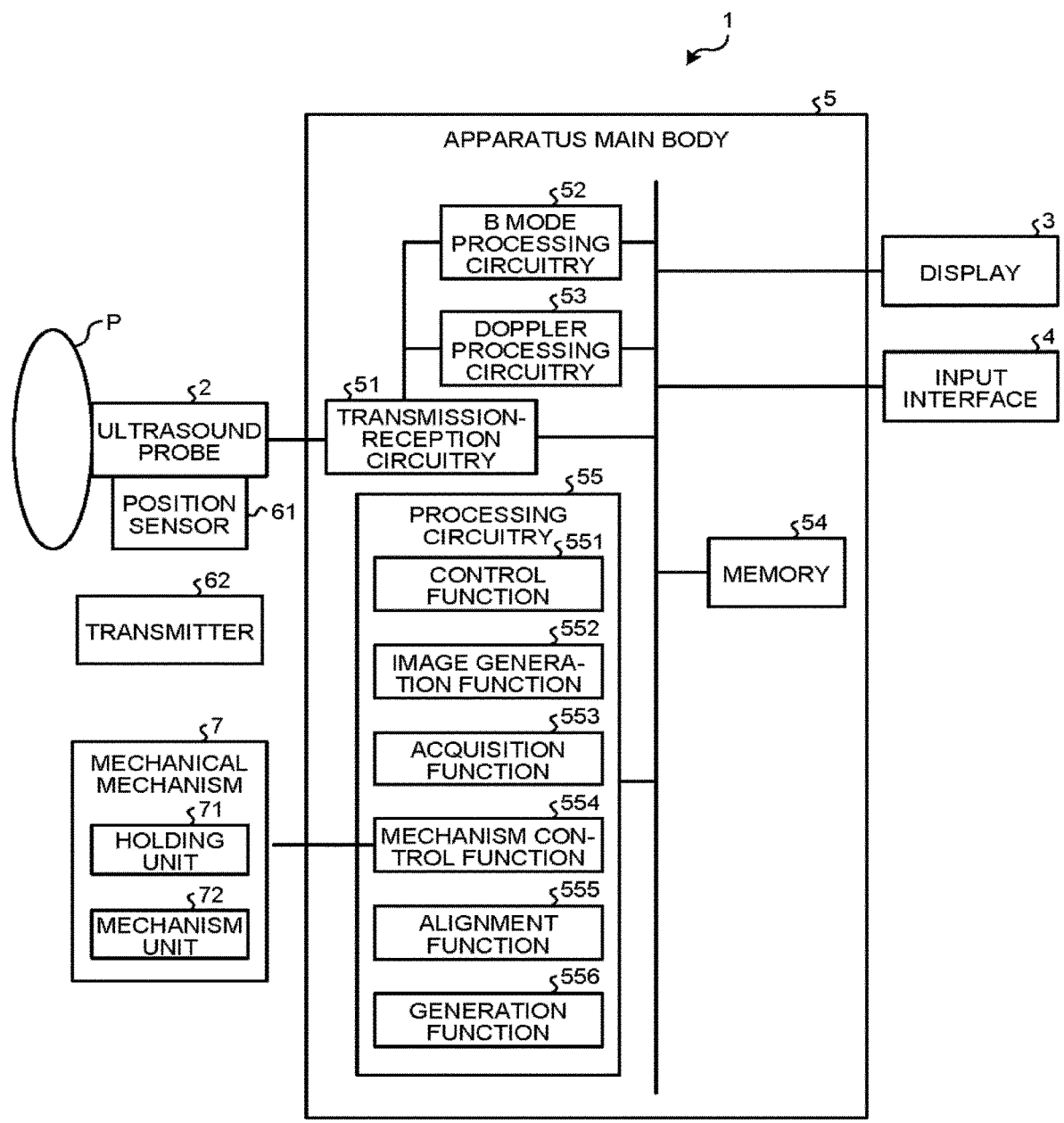
FIG. 1 is a block diagram illustrating an exemplary configuration of an ultrasound diagnostic apparatus according to a first embodiment.

The following first describes an ultrasound diagnostic apparatus according to a first embodiment. FIG. 1 is a block diagram illustrating an exemplary configuration of an ultrasound diagnostic apparatus 1 according to the first embodiment. As illustrated in FIG. 1, the ultrasound diagnostic apparatus 1 according to the present embodiment includes an ultrasound probe 2, a display 3, an input interface 4, and an apparatus main body. The ultrasound probe 2, the display 3, and the input interface 4 are connected with an apparatus main body 5 to perform communication therebetween. In addition, in the ultrasound diagnostic apparatus 1 according to the present embodiment, a position sensor 61, a transmitter 62, and a mechanical mechanism 7 are connected with the apparatus main body 5 to perform communication therebetween. The configuration including the ultrasound diagnostic apparatus 1 and the mechanical mechanism 7 is an exemplary ultrasound automatic scanning system according to the present application.

The ultrasound probe 2 is connected with transmission-reception circuitry 51 included in the apparatus main body 5. For example, the ultrasound probe 2 includes a plurality of piezoelectric transducer elements in a probe body. The piezoelectric transducer elements generate an ultrasonic wave based on a drive signal supplied from the transmission-reception circuitry 51. The ultrasound probe 2 receives a reflected wave from a subject P and converts the received wave into an electric signal. In the probe body, the ultrasound probe 2 also includes a matching layer provided to each piezoelectric transducer element, and a backing material or the like for preventing ultrasonic wave propagation beyond the piezoelectric transducer element. The ultrasound probe 2 is detachably connected with the apparatus main body 5. For example, the ultrasound probe 2 is an ultrasound probe of a sector type, a linear type, or a convex type.

When ultrasonic wave is transmitted from the ultrasound probe 2 to the subject P, the transmitted ultrasonic wave is sequentially reflected by discontinuous surfaces of acoustic impedance at body tissue of the subject P and received as a reflected wave signal by the piezoelectric transducer elements included in the ultrasound probe 2. The amplitude of the received reflected wave signal depends on acoustic impedance difference at each discontinuous surface at which the ultrasonic wave is reflected. The reflected wave signal when the transmitted ultrasonic wave pulse is reflected by moving blood current or a surface such as a cardiac wall is subjected to frequency shift due to the Doppler effect, depending on a speed component of the moving object in the ultrasonic wave transmission direction.

The present embodiment is applicable to a case in which the subject P is two-dimensionally scanned by the ultrasound probe 2 as a one-dimensional ultrasound probe in which the piezoelectric transducer elements are disposed in a line, and a case in which the subject P is three-dimensionally scanned by the ultrasound probe 2 in which the piezoelectric transducer elements of the one-dimensional ultrasound probe are mechanically swung or by the ultrasound probe 2 as a two-dimensional ultrasound probe in which the piezoelectric transducer elements are two-dimensionally disposed in lattice.

In the ultrasound probe 2, the position sensor 61 is mounted on the probe body to acquire position information. The ultrasound probe 2 is moved with the probe body held by the mechanical mechanism 7 while an ultrasonic-wave transmission-reception surface is pointed to the subject. Details of these components will be described later.

The display 3 displays a graphical user interface (GUI) through which an operator of the ultrasound diagnostic apparatus 1 inputs various setting requests by using the input interface 4, and displays an ultrasound image or the like generated in the apparatus main body 5. The display 3 also displays various messages and display information to notify the operator of the processing status of the apparatus main body 5 and a processing result. In addition, the display 3 may include a speaker to output voice.

The input interface 4 is achieved by, for example, a track ball, a switch button, a mouse, a keyboard, a touch pad on which an input operation can be performed through touching on an operation surface, a touch monitor that integrates a display screen and a touch pad, non-contact input circuitry using an optical sensor, or voice input circuitry, which are used to perform setting of a predetermined position (for example, an interest region) and the like. The input interface 4 is connected with processing circuitry 55 to be described later to convert an input operation received from the operator into an electric signal and output the electric signal to the processing circuitry 55. In the present specification, the input interface 4 does not always need to include a physical operation member such as a mouse or a keyboard. Examples of the input interface include an electric signal processing circuit configured to receive an electric signal corresponding to an input operation from an external input instrument provided separately from the device and output the electric signal to the processing circuitry 55.

The position sensor 61 and the transmitter 62 are devices for acquiring position information of the ultrasound probe 2. For example, the position sensor 61 is a magnetic sensor attached to the ultrasound probe 2. For example, the transmitter 62 is a device disposed at an optional position and configured to form an outward magnetic field centered at the transmitter 62.

The position sensor 61 detects the three-dimensional magnetic field formed by the transmitter 62. Then, the position sensor 61 calculates, based on information of the detected magnetic field, the position (coordinates) and the direction (angle) of the position sensor 61 in a space having an origin at the transmitter 62, and transmits the calculated position and direction to the processing circuitry 55 to be described later. The three-dimensional position information (position and direction) of the position sensor 61 transmitted to the processing circuitry 55 is converted as appropriate into the position information of the ultrasound probe 2 (for example, information of the central position of the ultrasonic-wave transmission-reception surface of the ultrasound probe 2) or position information of the range of scanning by the ultrasound probe 2 and is used.

The present embodiment is also applicable to a case in which the position information of the ultrasound probe 2 is acquired by a system other than the above-described position detection system. For example, the present embodiment is applicable to a case in which the position information of the ultrasound probe 2 is acquired by using a gyro sensor, an acceleration sensor, or the like.

The mechanical mechanism 7 includes a holding unit 71 configured to hold the probe body of the ultrasound probe 2, and a mechanism unit 72 configured to move the ultrasound probe 2 to a desired position on the body surface of the subject. Specifically, the mechanical mechanism 7 moves the ultrasound probe 2 held by the holding unit 71 to a desired position through motion of the mechanism unit 72. For example, the mechanical mechanism 7 moves the ultrasound probe 2 in accordance with control of the apparatus main body 5. The following describes an exemplary mechanical mechanism with reference to FIG. 2. The mechanical mechanism 7 illustrated in FIG. 2 is merely exemplary, and the embodiment is not limited thereto.

Figure 2:
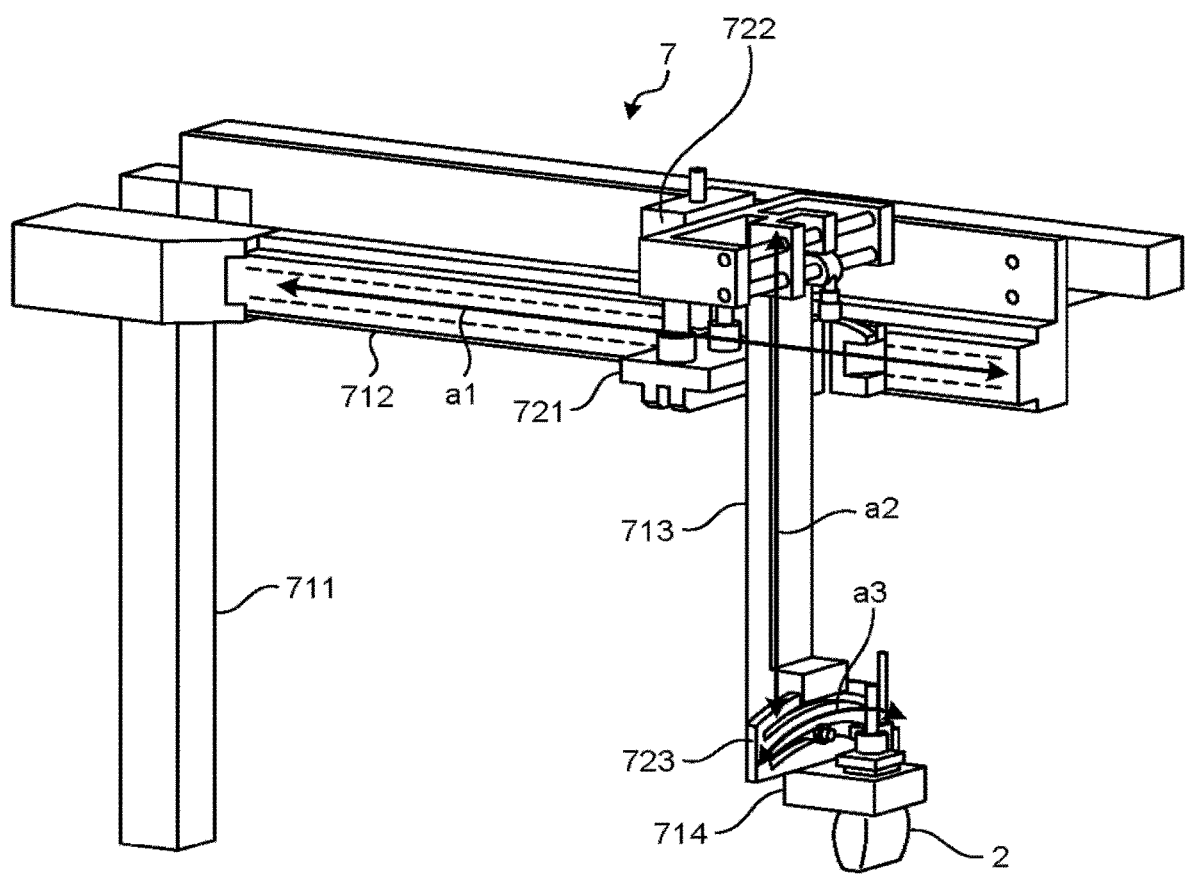
FIG. 2 is an exterior diagram illustrating an exemplary mechanical mechanism according to the first embodiment.

FIG. 2 is an exterior diagram illustrating an exemplary mechanical mechanism 7 according to the first embodiment.

As illustrated in FIG. 2, the mechanical mechanism 7 includes the holding unit 71 including a first holding unit 711, a second holding unit 712, a third holding unit 713, and a fourth holding unit 714, and includes the mechanism unit 72 including a first mechanism unit 721, a second mechanism unit 722, and a third mechanism unit 723. The holding unit 71 is a cast metal made of, for example, aluminum, and includes a junction part for joining holding units, an engagement part to be engaged with the mechanism unit 72, and a probe holder holding the ultrasound probe 2. The mechanism nit 72 includes a drive unit such as a motor or an actuator, and an engagement part for engagement with a holding unit.

For example, the first holding unit 711 has, in the longitudinal direction, one end joined with a base part (not illustrated) supporting the entire mechanical mechanism 7, and the other end joined with the second holding unit 712. Accordingly, the first holding unit 711 supports all members directly or indirectly held by the second holding unit 712. The second holding unit 712 has, in the longitudinal direction, one end joined with the first holding unit 711, and engaged with the first mechanism unit 721 so that the first mechanism unit 721 is slidable in the longitudinal direction. For example, the second holding unit 712 includes a rail extending in the longitudinal direction and engaged with the first mechanism unit 721, and slidably holds the first mechanism unit 721 on the rail.

When the second holding unit 712 is joined with the first holding unit 711 so that the longitudinal direction of the second holding unit 712 is horizontal as illustrated in FIG. 2, the first mechanism unit 721 slides in the horizontal direction illustrated with Arrow a1. The first mechanism unit 721 is held by the second holding unit 712 through engagement and moves in the longitudinal direction of the second holding unit 712 by the drive power of the drive unit such as a motor or an actuator. For example, the first mechanism unit 721 is engaged with the rail of the second holding unit 712 and slides on the rail by the drive power of the drive unit based on control of the apparatus main body 5. The first mechanism unit 721 is joined with the second mechanism unit 722.

The second mechanism unit 722 is held by the second holding unit 712 while being joined with the first mechanism unit 721. The second mechanism unit 722 holds the third holding unit 713 while being engaged with the third holding unit 713 so that the third holding unit 713 is slidable. In other words, the second mechanism unit 722 moves in the longitudinal direction of the second holding unit 712 and slides the third holding unit 713 along with gilding of the first mechanism unit 721. The second mechanism unit 722 slides the third holding unit 713 in a direction orthogonal to the moving direction of the first mechanism unit 721. For example, the second mechanism unit 722 slides the third holding unit 713 in the vertical direction illustrated with Arrow a2 by the drive power of the drive unit based on control of the apparatus main body 5.

The third holding unit 713 has, in the longitudinal direction, one end engaged with the second mechanism unit 722 and slides on the second mechanism unit 722. For example, the third holding unit 713 includes, in the longitudinal direction, a rail to be engaged with the second mechanism unit 722, and slides on the second mechanism unit 722 in the vertical direction illustrated with Arrow a2. The third holding unit 713 has the other end engaged with the third mechanism unit 723. The third holding unit 713 holds the third mechanism unit 723 so that the third mechanism unit 723 rotates about the longitudinal direction of the second holding unit 712. For example, the third holding unit 713 holds the third mechanism unit 723 so that the third mechanism unit 723 is rotatable in the direction illustrated with Arrow a3.

The third mechanism unit 723 is held by the third holding unit 713 while being engaged with the third holding unit 713. The third mechanism unit 723 is joined with the fourth holding unit 714. For example, the third mechanism unit 723 rotates in the direction illustrated with Arrow a3 by the drive power of the drive unit based on control of the apparatus main body 5 while holding the fourth holding unit 714 (without changing the orientation of the fourth holding unit 714). Accordingly, the third mechanism unit 723 can change the angle of the ultrasound probe 2 held by the fourth holding unit 714.

The fourth holding unit 714 is joined with the third mechanism unit 723 and holds the ultrasound probe 2. For example, as illustrated in FIG. 2, the fourth holding unit 714 holds the ultrasound probe 2 so that the plane direction of the ultrasonic-wave transmission-reception surface of the ultrasound probe is orthogonal to the longitudinal direction of the third holding unit 713.

As described above, the mechanical mechanism 7 can move the ultrasound probe 2 held by the fourth holding unit 714 in the directions illustrated with Arrow a1, Arrow a2, and Arrow a3 through movement by the first mechanism unit 721, movement by the second mechanism unit 722, and movement by the third mechanism unit 723. In other words, the mechanical mechanism 7 can move the ultrasound probe 2 in the horizontal direction and the vertical direction and change the angle of the ultrasound probe 2. The mechanical mechanism 7 illustrated in FIG. 2 is an exemplary mechanical mechanism, and the mechanical mechanism is not limited to that illustrated in FIG. 2. For example, the mechanical mechanism 7 may include a mechanism unit configured to move the ultrasound probe 2 in a direction orthogonal to Arrow a1 and orthogonal to Arrow a2.

Returning to FIG. 1, the apparatus main body 5 includes the transmission-reception circuitry 51, B mode processing circuitry 52, Doppler processing circuitry 53, a memory 54, and the processing circuitry 55. In the ultrasound diagnostic apparatus 1 illustrated in FIG. 1, each processing function is stored in the form of computer-executable program in the memory 54. The transmission-reception circuitry 51, the B mode processing circuitry 52, the Doppler processing circuitry 53, and the processing circuitry 55 are each a processor configured to achieve a function corresponding to a computer program by reading and executing the computer program from the memory 54. In other words, each circuitry having read a computer program has a function corresponding to the read computer program.

The transmission-reception circuitry 51 includes a pulse generator, a transmission delay circuitry, a pulser, and the like, and supplies the drive signal to the ultrasound probe 2. The pulse generator repeatedly generates a rate pulse for forming transmission ultrasonic wave at a predetermined rate frequency. The transmission delay circuitry provides, to each rate pulse generated by the pulse generator, a delay time for each piezoelectric transducer element necessary for converging, into a beam form, an ultrasonic wave generated from the ultrasound probe 2 and for determining transmission directionality. The pulser applies the drive signal (drive pulse) to the ultrasound probe 2 at a timing based on the rate pulse. Specifically, the transmission delay circuitry optionally adjusts the transmission direction of ultrasonic wave transmitted from a piezoelectric transducer element surface by changing the delay time provided to each rate pulse.

The transmission-reception circuitry 51 has a function of instantaneously changing transmission frequency, transmission drive voltage, and the like to execute a predetermined scanning sequence based on an instruction from the processing circuitry 55 to be described later. In particular, change of the transmission drive voltage is achieved by a linear-amplifier oscillation circuitry capable of instantaneously switching the voltage, or a mechanism capable of electrically switching a plurality of power source units.

The transmission-reception circuitry 51 also includes a pre-amplifier, an analog/digital (A/D) converter, a reception delay circuitry, an adder, and the like, and generates reflected wave data by performing various kinds of processing on a reflected wave signal received by the ultrasound probe 2. The pre-amplifier amplifies the reflected wave signal for each channel. The A/D converter performs A/D conversion of the amplified reflected wave signal. The reception delay circuitry provides a delay time necessary for determining reception directionality. The adder generates reflected wave data by performing addition processing of the reflected wave signal processed by the reception delay circuitry. Addition processing by the adder enhances a reflection component from a direction in accordance with the reception directionality of the reflected wave signal, and forms a comprehensive beam of ultrasonic wave transmission and reception with the reception directionality and the transmission directionality.

The B mode processing circuitry 52 receives the reflected wave data from the transmission-reception circuitry 51, performs logarithmic amplification, envelope detection processing, and the like on the data, and generates data (B mode data) in which signal intensity is represented in brightness as luminance.

The Doppler processing circuitry 53 performs frequency analysis of speed information in the reflected wave data received from the transmission-reception circuitry 51, extracts blood current, tissue, and a contrast-dye echo component based on the Doppler effect, and generates data (Doppler data) obtained by extracting moving object information such as speed, dispersion, and power at a number of points. A moving object in the present embodiment is fluid such as blood flowing in a blood vessel or lymph flowing in a lymph vessel.

The B mode processing circuitry 52 and the Doppler processing circuitry 53 can process both two-dimensional reflected wave data and three-dimensional reflected wave data. Specifically, the B mode processing circuitry 52 generates two-dimensional B mode data from two-dimensional reflected wave data, and generates three-dimensional B mode data from three-dimensional reflected wave data. The Doppler processing circuitry 53 generates two-dimensional Doppler data from two-dimensional reflected wave data, and generates three-dimensional Doppler data from three-dimensional reflected wave data. The three-dimensional B mode data is data in which a luminance value in accordance with reflection intensity from a reflection source positioned at each of a plurality of points (sample points) set on each scanning line in the three-dimensional scanning range is allocated to the point. The three-dimensional Doppler data is data in which a luminance value in accordance with the value of blood current information (speed, dispersion, and power) is allocated to each of a plurality of points (sample points) set on each scanning line in the three-dimensional scanning range.

The memory 54 stores display image data generated by the processing circuitry 55. The memory 54 may also store data generated by the B mode processing circuitry 52 and the Doppler processing circuitry 53. The memory 54 also stores control programs for performing ultrasonic wave transmission and reception, image processing, and display processing, and various kinds of data such as diagnosis information (for example, a patient ID and doctor comments), diagnosis protocols, and various body marks. The memory 54 also stores a scanning path generated by the processing circuitry 55. Details of the scanning path will be described later.

The processing circuitry 55 controls the entire processing at the ultrasound diagnostic apparatus 1. Specifically, the processing circuitry 55 performs various kinds of processing by reading computer programs corresponding to a control function 551, an image generation function 552, an acquisition function 553, a mechanism control function 554, an alignment function 555, and a generation function 556, which are illustrated in FIG. 1, from the memory 54 and executing the computer programs. The generation function 556 is an exemplary generation unit.

For example, the processing circuitry 55 controls processing at the transmission-reception circuitry 51, the B mode processing circuitry 52, and the Doppler processing circuitry 53 based on various setting requests input by the operator through the input interface 4, and various kinds of control programs and various kinds of data read from the memory 54. The processing circuitry 55 controls the display to display display ultrasound image data stored in the memory 54. The processing circuitry 55 controls the display 3 to display a processing result. For example, the processing circuitry 55 controls the entire device by reading and executing the computer program corresponding to the control function 551, and controls the above-described processing.

The image generation function 552 generates ultrasound image data from data generated by the B mode processing circuitry 52 and the Doppler processing circuitry 53. Specifically, the image generation function 552 generates, from two-dimensional B mode data generated by the B mode processing circuitry 52, B mode image data in which the intensity of reflected wave is represented in luminance. The B mode image data is data in which the shape of tissue in a region in which ultrasound scanning is performed is visualized. The image generation function 552 also generates Doppler image data representing moving object information from two-dimensional Doppler data generated by the Doppler processing circuitry 53. The Doppler image data is speed image data, dispersion image data, power image data, or combination of these image data. The Doppler image data represents fluid information related to fluid flowing in the region in which ultrasound scanning is performed.

The image generation function 552 typically generates display ultrasound image data by converting (scanning conversion) a scanning line signal string of ultrasound scanning into a scanning line signal string in a video format such as the video format of television. Specifically, the image generation function 552 generates display ultrasound image data by performing coordinate transform in accordance with the form of ultrasound scanning performed by the ultrasound probe 2. Examples of various kinds of image processing performed by the image generation function 552 other than the scanning conversion include image processing (smoothing processing) of regenerating an image of an averaged luminance value by using a plurality of image frames after the scanning conversion, and image processing (edge enhancement processing) using a differential filter in an image. In addition, the image generation function 552 synthesizes the ultrasound image data with character information of various kinds of parameters, scales, body marks, and the like.

In other words, the B mode data and the Doppler data are the ultrasound image data before the scanning conversion processing, and data generated by the image generation function 552 is the display ultrasound image data after the scanning conversion processing. The B mode data and the Doppler data are also called raw data.

In addition, the image generation function 552 generates three-dimensional B mode image data by performing coordinate transform of the three-dimensional B mode data generated by the B mode processing circuitry 52. The image generation function 552 also generates three-dimensional Doppler image data by performing coordinate transform of the three-dimensional Doppler data generated by the Doppler processing circuitry 53. The three-dimensional B mode data and the three-dimensional Doppler data are volume data before the scanning conversion processing. In other words, the image generation function 552 generates "the three-dimensional B mode image data and the three-dimensional Doppler image data" as "volume data that is three-dimensional ultrasound image data".

In addition, the image generation function 552 may perform rendering processing on the volume data to generate various two-dimensional image data for displaying the volume data on the display 3. The acquisition function 553 acquires probe position information indicating the position and direction of the ultrasound probe 2. The mechanism control function 554 controls the mechanical mechanism 7. The alignment function 555 performs positioning between the coordinate system of the probe position information and the coordinate system of the mechanical mechanism 7. The generation function 556 generates a scanning path. Details of processing performed by the acquisition function 553, the mechanism control function 554, the alignment function 555, and the generation function 556 will be described later.

The entire configuration of the ultrasound diagnostic apparatus 1 according to the first embodiment has been described above. With this configuration, the ultrasound diagnostic apparatus 1 according to the first embodiment allow easy generation of a scanning path indicating the movement locus of the ultrasound probe. Specifically, the ultrasound diagnostic apparatus 1 according to the first embodiment allows easy generation of a scanning path when the subject is scanned by the mechanical mechanism 7 by performing provisional scanning on the subject and acquiring the distance between the body surface of the subject and the ultrasound probe 2 from a result of the provisional scanning.

As described above, a recently disclosed technology in ultrasound diagnosis performs scanning while an ultrasound probe is moved by a robot. For example, in a known technology, position information of the body surface of a subject is acquired from a picture obtained by capturing the subject with a camera, and a scanning path when the ultrasound probe is moved by a robot is generated by using the acquired position information. However, in this technology, since the picture is two-dimensional information, a significantly large number of pictures obtained through image capturing in various kinds of directions are needed to generate a three-dimensional scanning path, and a complex algorithm is used to acquire position information from the pictures. In the ultrasound diagnostic apparatus 1 according to the first embodiment, the mechanical mechanism 7 holds and moves an ultrasound probe while the ultrasonic-wave transmission-reception surface of the ultrasound probe is pointed to a subject. Then, the generation function 556 generates, based on information of the positional relation between the ultrasound probe moved by the mechanical mechanism 7 and the subject, the scanning path of the ultrasound probe 2 when ultrasound scanning is executed on the subject, thereby allowing easy generation of the scanning path.

The following describes details of the ultrasound diagnostic apparatus 1 according to the first embodiment. The acquisition function 553 temporally acquires the probe position information of the ultrasound probe 2 based on a signal from the position sensor 61 mounted on the ultrasound probe 2. In other words, the acquisition function 553 temporally acquires the position information (coordinate information) of the position sensor 61. The acquisition function 553 can convert the signal received from the position sensor 61 into the coordinates of an optional position on the ultrasound probe 2 based on information of a position at which the position sensor 61 is mounted on the ultrasound probe 2 (information of the positional relation between the ultrasound probe 2 and the position sensor 61). For example, the acquisition function 553 can convert the position information (coordinate information) of the position sensor 61 into information (coordinate information) of the central position of the ultrasonic-wave transmission-reception surface of the ultrasound probe 2 based on the information of the positional relation between the ultrasound probe 2 and the position sensor 61.

For example, when a magnetic sensor is used as the position sensor 61, the acquisition function 553 acquires position information (position and orientation) temporally acquired by the position sensor 61 in a three-dimensional magnetic field (coordinate system of the probe position information) formed by the transmitter 62. Then, the acquisition function 553 transmits the acquired position information at each time to the alignment function 555. The acquisition function 553 also transmits the acquired position information at each time to the generation function 556. For example, the acquisition function 553 acquires the position information at each time acquired by the position sensor 61 mounted on the ultrasound probe 2 held by the fourth holding unit 714, and transmits the acquired position information to the alignment function and the generation function 556.

The mechanism control function 554 controls movement of the mechanism unit 72 of the mechanical mechanism 7 by transmitting a control signal to the drive unit included in the mechanism unit 72. For example, the mechanism control function 554 controls the drive unit of the first mechanism unit 721 by transmitting a control signal to the first mechanism unit 721, thereby controlling sliding of the first mechanism unit 721 in the direction illustrated with Arrow a1. For example, the mechanism control function 554 controls the drive unit of the second mechanism unit 722 by transmitting a control signal to the second mechanism unit 722, thereby controlling sliding of the third holding unit 713 in the direction illustrated with Arrow a2. For example, the mechanism control function 554 controls the drive unit of the third mechanism unit 723 by transmitting a control signal to the third mechanism unit 723, thereby controlling rotation of the third mechanism unit 723 in the direction illustrated with Arrow a3.

Then, the mechanism control function 554 transmits control information at each time to the alignment function 555. Specifically, the mechanism control function 554 transmits information of the position of each mechanism unit in the coordinate system of the mechanical mechanism 7 at each time to the alignment function 555. The mechanism control function 554 also transmits the control information at each time to the generation function 556. In addition, the mechanism control function 554 controls the mechanical mechanism 7 based on the scanning path generated by the generation function 556, which will be described later.

The alignment function 555 performs positioning between the coordinate system of the probe position information and the coordinate system of the mechanical mechanism 7. Specifically, the alignment function 555 synchronizes, based on time information, the position information at each time received from the acquisition function 553 and the control information at each time received from the mechanism control function 554. For example, the alignment function 555 associates the position information (three-dimensional coordinate information) of the position sensor 61 mounted on the ultrasound probe 2 held by the fourth holding unit 714 at "time t1" with the control information of the mechanical mechanism 7 (three-dimensional coordinate information of an optional part of the mechanical mechanism 7) at "time t1". The three-dimensional coordinate information of an optional part of the mechanical mechanism 7 is, for example, the position of the fourth holding unit 714 holding the ultrasound probe 2, and is expressed in the drive amounts of the first mechanism unit 721, the second mechanism unit 722, and the third mechanism unit 723.

Specifically, the alignment function 555 associates the position information of the position sensor 61 with information of the drive amounts of the first mechanism unit. 721, the second mechanism unit 722, and the third mechanism unit 723 at "time t1". Accordingly, the alignment function 555 can associate the position information of the position sensor 61 with the drive state of each mechanism unit. Then, the alignment function 555 transmits the associated information to the generation function 556.

The generation function 556 generates, based on information of the positional relation between the ultrasound probe 2 to be moved by the mechanical mechanism 7 and the subject, a scanning path indicating the locus of movement of the ultrasound probe 2 when ultrasound scanning is executed on the subject. Specifically, the generation function 556 generates the scanning path based on the positional relation between the body surface of a scanning target site of the subject and the ultrasound probe 2, which is acquired by placing the scanning target site at a predetermined position and operating the mechanical mechanism 7 once for the placed scanning target site. For example, the generation function 556 acquires the distance between the body surface of the subject and the ultrasonic-wave transmission-reception surface of the ultrasound probe 2 based on reflected wave data collected as the ultrasound probe 2 is moved relative to the subject in a non-contact manner by the mechanical mechanism 7, and generates the scanning path based on the acquired distance.

Figure 3:
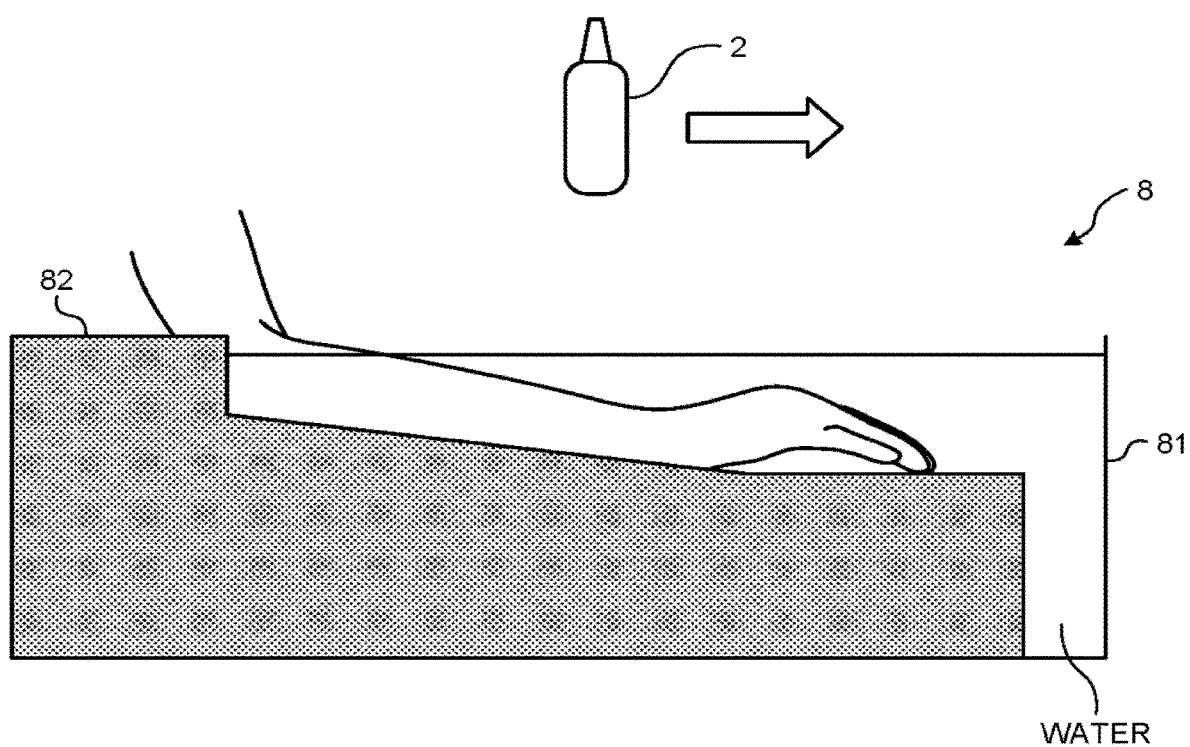
FIG. 3 is a diagram for describing an exemplary placement table for a scanning target site according to the first embodiment.

In the ultrasound diagnostic apparatus 1 according to the first embodiment, reflected wave data of a scanning target site is collected as the mechanical mechanism 7 moves the ultrasound probe relative to the subject in a non-contact manner. In the first embodiment, water is used as an acoustic medium so that ultrasonic wave can be transmitted and received while the ultrasound probe 2 does not contact the body surface of the subject. FIG. 3 is a diagram for describing an exemplary placement table 8 for a scanning target site according to the first embodiment. FIG. 3 illustrates an exemplary placement table when the scanning target site ranges from a forearm to the hand.

For example, as illustrated in FIG. 3, the placement table 8 includes a water tank 81 and an armrest 82, the water tank 81 being filled with water. The armrest 82 includes an elbow rest part and a slope part gradually tilted downward from the elbow rest part. As illustrated in FIG. 3, the water tank 81 of the placement table 8 is filled with water so that, when an arm is placed on the armrest 82, a part ranging from the forearm to the hand is placed in the water. Then, the mechanical mechanism 7 is disposed so that the ultrasound probe 2 is movable relative to the arm placed on the placement table 8 in the direction illustrated with the arrow in FIG. 3. For example, the mechanical mechanism 7 is disposed so that the longitudinal direction of the second holding unit 712 illustrated in FIG. 2 is parallel to the longitudinal direction of the forearm placed on the placement table 8 and the scanning target site is scanned by an ultrasonic wave transmitted from the ultrasound probe 2 held by the fourth holding unit 714.

Then, when the scanning target site is to be scanned, the ultrasound probe 2 is placed in the water in the water tank 81 and transmits and receives an ultrasonic wave without contacting the body surface of the scanning target site. For example, the third holding unit 713 is slid in the vertical direction by drive of the second mechanism unit 722 so that the ultrasound probe 2 is placed in the water in the water tank 81 and the ultrasound probe 2 does not contact the b surface.

The placement able 8 may be provided with a concave portion or a convex portion at the armrest 82 to stabilize the placement state of the scanning target site. Specifically, the armrest 82 may be provided with a concave portion or a convex portion for fixing the scanning target site so that, when the subject places the scanning target site on the placement table 8, the scanning target site is constantly placed substantially at an identical position on the placement table 8.

Figure 4A:
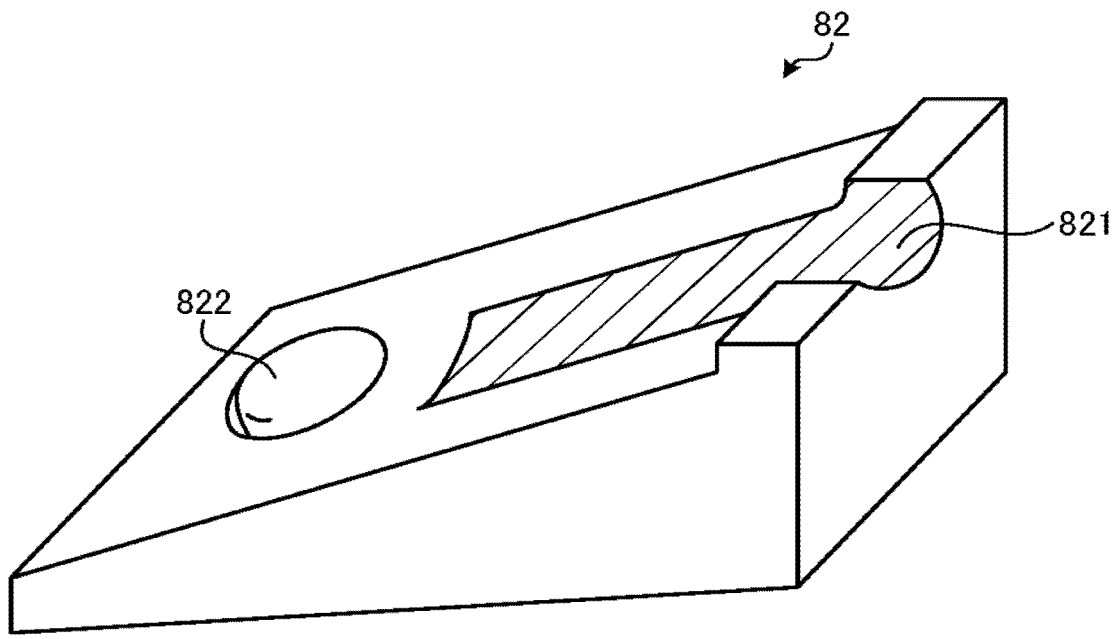
FIG. 4A is a diagram illustrating an exemplary armrest according to the first embodiment.
Figure 4B:
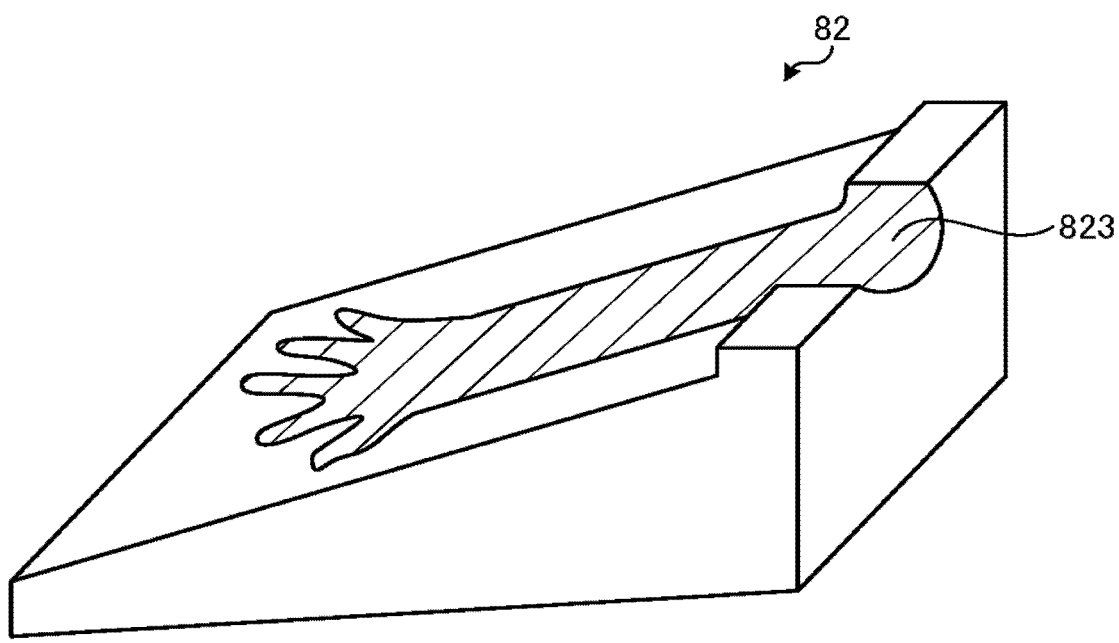
FIG. 4B is a diagram illustrating another exemplary armrest according to the first embodiment.

FIGS. 4A and 4B are each a diagram illustrating an exemplary armrest 82 according to the first embodiment. For example, as illustrated in FIG. 4A, the armrest 82 includes a concave portion 821 on which the part from the elbow to the forearm is placed from the elbow rest part to the slope part, and a convex portion 822 that supports the hand. When the armrest 82 is used, for example, the subject can constantly place the arm substantially at an identical position by placing the part from the elbow to the forearm on the concave portion 821 and by lightly grasping the convex portion 822.

Alternatively, for example, as illustrated in FIG. 4B, the armrest 82 may include a concave portion 823 on which the part from the elbow to the hand is placed from the elbow rest part to the slope part. The concave portion 823 includes a concave portion in a hand shape, and for example, the subject can constantly place the arm substantially at an identical position by placing the part from the elbow to the hand in the concave portion 823.

In the first embodiment, scanning is executed in a non-contact manner by the mechanical mechanism 7 while an arm is placed on the placement table 8 thus configured. In the first embodiment, first, the provisional scanning is executed to acquire the positional relation between the scanning target site placed on the placement table 8 and the ultrasound probe. For example, after the scanning target site (from the forearm to the hand) is placed on the placement table 8 and the mechanical mechanism 7 holding the ultrasound probe 2 is disposed, the acquisition function 553 acquires the position information of the position sensor 61 after the disposition and transmits the acquired position information to the alignment function 555. In addition, the mechanism control function 554 transmits the current drive amount of each mechanism unit of the mechanical mechanism 7 to the alignment function 555. The alignment function 555 performs positioning between the coordinate system of the probe position information and the coordinate system of the mechanical mechanism 7 by associating the position information of the position sensor 61 with information of the drive amounts. Then, the alignment function 555 transmits information of the positioning to the generation function 556.

After the above-described positioning ends, the mechanism control function 554 controls the mechanism unit 72 of the mechanical mechanism 7 so that the ultrasound probe 2 is disposed in the water tank 81 of the placement table 8 (the ultrasound probe 2 is disposed at a position where the provisional scanning is started). In this state, the acquisition function 553 acquires the position information temporally acquired by the position sensor 61 while the mechanical mechanism 7 is driven, and transmits the acquired position information to the generation function 556. Accordingly, the generation function 556 can constantly acquire the current position information of the position sensor 61. In addition, the mechanism control function 554 transmits the drive amount of each mechanism unit to the generation function 556 at each drive of the mechanical mechanism 7. Accordingly, the generation function 556 can constantly acquire the drive state of the mechanical mechanism 7.

At the position where the provisional scanning is started, the ultrasound probe 2 is in the water in the water tank 81 and the ultrasound probe 2 does not contact the body surface. For example, at the position where the provisional scanning is started, the ultrasound probe 2 is in the water on the elbow rest side of the armrest 82 and the ultrasound probe 2 does not contact the body surface. The disposition of the ultrasound probe 2 at the position may be executed, for example, when the mechanism control function 554 is controlled in accordance with an operation by the operator through the input interface 4, or may be executed by the mechanism control function 554 so that the disposition is made at a position set in advance by taking into account the size of the placement table 8 and the like.

Then, when the ultrasound probe 2 is disposed at the position where the provisional scanning is started, the control function 551 and the mechanism control function 554 perform control to execute the provisional scanning. For example, the mechanism control function 554 performs control to drive only the drive unit of the first mechanism unit 721, thereby controlling the ultrasound probe 2 to slide in the horizontal direction without changing the position of the ultrasound probe 2 in the vertical direction. Specifically, the mechanism control function 554 slides the ultrasound probe 2 in the direction from the forearm to the hand. The mechanism control function 554 transmits, to the generation function 556, the drive amount of the drive unit of the first mechanism unit 721 at each time during the drive.

The control function 551 controls the transmission-reception circuitry 51 to repeatedly transmit ultrasonic wave from the ultrasound probe 2 and repeatedly receive reflected wave during the sliding of the ultrasound probe 2 by the mechanical mechanism 7. Then, the image generation function 552 generates ultrasound image data at each time based on reflected wave data temporally generated by the transmission-reception circuitry 51. In addition, the image generation function 552 transmits the generated ultrasound image data at each time to the generation function 556. The acquisition function 553 may acquire the position information of the position sensor 61 at each time during the provisional scanning and transmit the acquired position information to the generation function 556.

The generation function 556 calculates the distance between the body surface of the scanning target site and the ultrasonic-wave transmission-reception surface of the ultrasound probe 2 by using the positioning information (information associating the probe position information and the drive amount information) received from the alignment function 555, the drive amount information at each time received from the mechanism control function 554 (or the position information at each time acquired from the acquisition function 553), and the ultrasound image data at each time received from the image generation function 552. Then, the generation function 556 generates a scanning path based on the calculated distance.

For example, the generation function 556 calculates the central position of the ultrasonic-wave transmission-reception surface of the ultrasound probe 2 in the coordinate system of the mechanical mechanism 7 from the drive amount information at each time received from the mechanism control function 554 and the positioning information. For example, the generation function 556 calculates the coordinates of the position sensor 61 in the coordinate system of the mechanical mechanism 7 from the drive amount information and the positioning information of the mechanical mechanism 7. Then, the generation function 556 converts the calculated coordinates of the position sensor 61 into the central coordinates of the ultrasonic-wave transmission-reception surface based on information of the attachment position of the position sensor 61 to the ultrasound probe 2. The generation function 556 calculates the central coordinates of the ultrasonic-wave transmission-reception surface in the coordinate system of the mechanical mechanism 7 at each time by performing the above-described processing on the drive amount information at each time.

The above-described coordinate conversion processing is omitted when the position information of the position sensor 61 is converted into the central position information of the ultrasonic-wave transmission-reception surface of the ultrasound probe 2 by the acquisition function 553, and the drive amount information of the mechanical mechanism 7 and the central position information of the ultrasonic-wave transmission-reception surface of the ultrasound probe 2 are associated with each other by the alignment function 555. In the above-described example, the central coordinates of the ultrasonic-wave transmission-reception surface in the coordinate system of the mechanical mechanism 7 at each time is calculated from the drive amount information of the mechanical mechanism 7 at each time by using the positioning information. However, the embodiment is not limited thereto. The drive amount information of the mechanical mechanism 7 at each time may be calculated from the coordinate information of the position sensor 61 (or the central coordinate information of the ultrasonic-wave transmission-reception surface after conversion) by using the positioning information.

Figure 5:
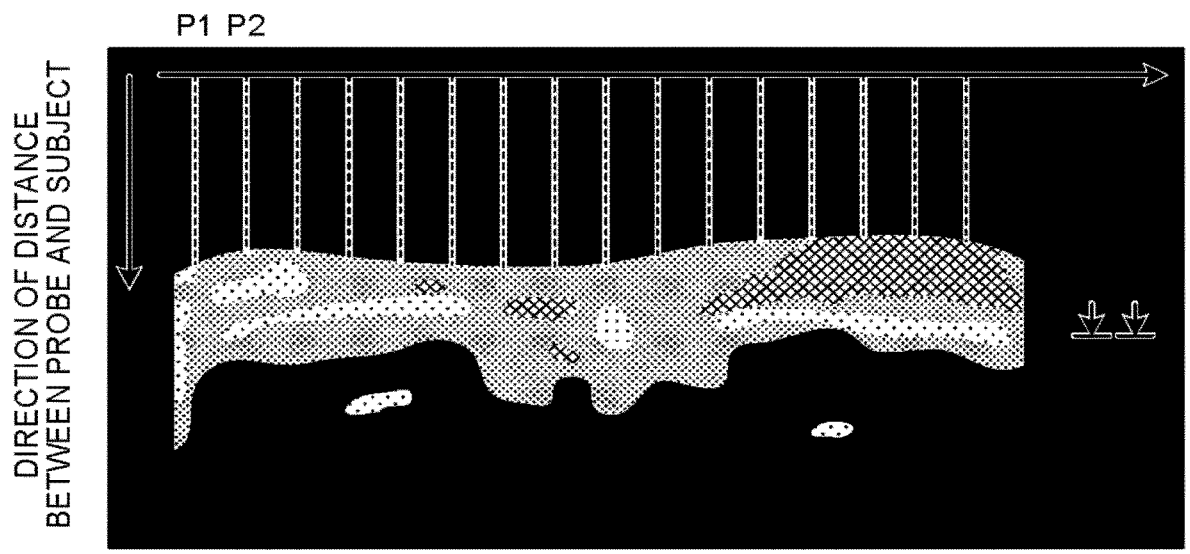
FIG. 5 is a diagram for describing exemplary processing by a generation function according to the first embodiment.

Having calculated the central coordinates of the ultrasonic-wave transmission-reception surface time in the coordinate system of the mechanical mechanism 7 at each time as described above, the generation function 556 calculates the distance between the transmission-reception surface and the body surface in the coordinate system of the mechanical mechanism 7 at each time during the provisional scanning by using the ultrasound image data at each time. FIG. 5 is a diagram for describing exemplary processing by the generation function 556 according to the first embodiment. FIG. 5 illustrates a cross-sectional view of ultrasound image data collected by the provisional scanning performed while the ultrasound probe 2 is slid in the direction from the forearm to the hand by drive of the first mechanism unit 721. In other words, FIG. 5 illustrates an image obtained by connecting a plurality of pieces of ultrasound image data collected by the ultrasound probe 2 being slid.

For example, the generation function 556 calculates the distance between the transmission-reception surface and the body surface from the central coordinates of the ultrasonic-wave transmission-reception surface at each time and the position of the body surface in the ultrasound image data collected at each time. For example, the generation function 556 extracts, based on time, the ultrasound image data corresponding to the central coordinates of the ultrasonic-wave transmission-reception surface at Position P1 in FIG. 5, and detects the body surface from the extracted ultrasound image data. The detection of the body surface in the ultrasound image data is executed by an existing optional method.

Then, the generation function 556 calculates the distance between the detected body surface and the ultrasonic-wave transmission-reception surface. Specifically, the generation function 556 calculates the distance between the body surface at Position P1 and the ultrasonic-wave transmission-reception surface. Similarly, the generation function 556 calculates the distance between the body surface at each position such as Position P2 and the ultrasonic-wave transmission-reception surface. In this manner, the generation function 556 calculates, for each position of the ultrasound probe 2 in the coordinate system of the mechanical mechanism 7, the distance between the body surface and the ultrasonic-wave transmission-reception surface during the provisional scanning.

Figure 6:
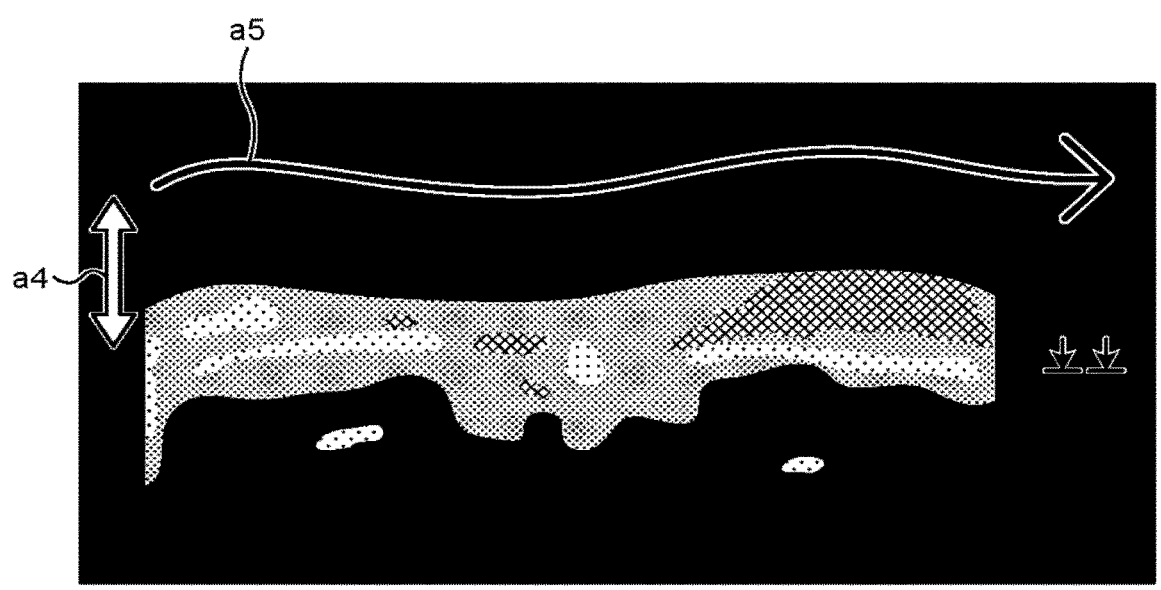
FIG. 6 is a diagram illustrating exemplary generation of a scanning path by the generation function according to the first embodiment.

In addition, the generation function 556 generates a scanning path based on the calculated distance. For example, the generation function 556 generates a scanning path, the distance of which from the body surface is equal to a predetermined distance. FIG. 6 is a diagram illustrating exemplary generation of a scanning path by the generation function 556 according to the first embodiment. For example, as illustrated in FIG. 6, the generation function 556 generates Scanning Path a5 on which the transmission-reception surface of the ultrasound probe 2 slides at a position separated from the body surface by "Distance a4".

In such a case, the generation function 556 calculates, for each position of the ultrasound probe 2, the coordinates of the position separated from the body surface by "Distance a4" based on the distance between the body surface and the ultrasonic-wave transmission-reception surface at the position of the ultrasound probe 2 in the coordinate system of the mechanical mechanism 7. Then, the generation function 556 connects the calculated coordinates to generate Scanning Path a5. In addition, the generation function 5 stores the generated Scanning Path a5 in the memory 54.

The above-described scanning path may be generated based on two-dimensionally collected ultrasound image data, or may be generated based on three-dimensionally collected ultrasound image data. Specifically, as described above, the generation function 556 can use two-dimensional ultrasound image data as illustrated in FIG. 5 calculate the distance between the body surface and the ultrasonic-wave transmission-reception surface for each position of the ultrasound probe 2 in the coordinate system of the mechanical mechanism 7, but may use ultrasound image data three-dimensionally collected in the provisional scanning to three-dimensionally extract the body surface and calculate the distance between each position on the body surface and the transmission-reception surface.

In such a case, for example, the generation function 556 calculates the distance between each position on the body surface and the transmission-reception surface for each position of the ultrasound probe 2 in the provisional scanning. Accordingly, the generation function 556 can acquire information such as irregularities and tilts of the body surface. Specifically, the generation function 556 can acquire stereoscopic information of the body surface (planer information of the body surface) and use the stereoscopic information to generate a scanning path.

Figure 7A:
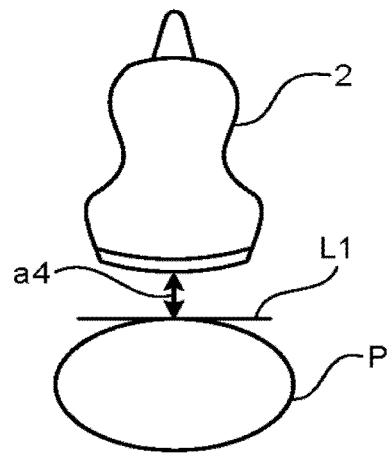
FIG. 7A is a diagram for describing the angle of the scanning path according to the first embodiment.
Figure 7B:
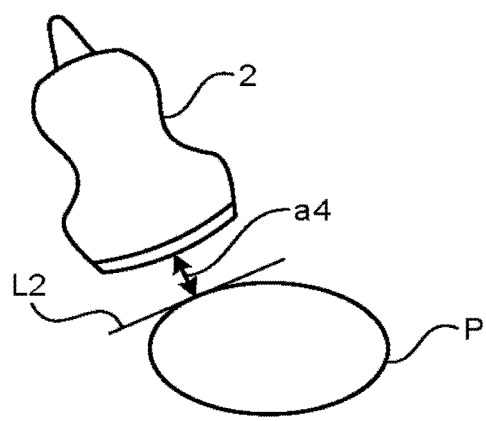
FIG. 7B is a diagram for describing the angle of the scanning path according to the first embodiment.
Figure 7C:
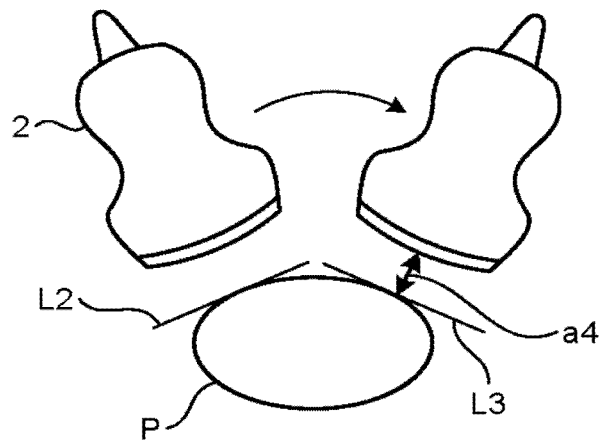
FIG. 7C is a diagram for describing the angle of the scanning path according to the first embodiment.

When having acquired the stereoscopic information of the body surface, the generation function 556 can generate a scanning path while taking into account the angle of the ultrasound probe 2 in addition to the distance from the body surface. FIGS. 7A to 7C are each a diagram for describing the angle of the scanning path according to the first embodiment. FIGS. 7A to 7C illustrate sections orthogonal to the longitudinal direction of the scanning target site (forearm).

When ultrasound image data is three-dimensionally collected, the generation function 556 can detect, for example, the body surface illustrated with an upper curved line of the section illustrated in FIG. 7A, FIG. 7A illustrates only the section, but in reality, information of the body surface in the depth direction in FIG. 7A is detected as well when the ultrasound image data is three-dimensionally collected as the ultrasound probe 2 is sliding in the longitudinal direction of the forearm. In other words, the generation function 556 can detect a curved surface of the body surface on the ultrasound probe 2 side.

Having detected the curved surface of the body surface in this manner, the generation function 556 calculates the distance between each position on the body surface and the transmission-reception surface of the ultrasound probe 2. When generating a scanning path while taking the angle of the ultrasound probe 2 into account, for example, the generation function 556 detects a position, the distance from which to the ultrasound probe 2 is shortest for each predetermined section on the body surface as illustrated in FIG. 7A, and sets the scanning path so that the distance to the detected position is equal to "Distance a4". Then, the generation function 556 sets the angle of the ultrasound probe 2 to be orthogonal to Tangent Line L1 at the position, the distance from which to the ultrasound probe 2 is shortest on the body surface.

The generation function 556 executes the above-described processing for each predetermined section in the longitudinal direction of the scanning target site (the forearm to the hand), thereby generating a scanning path from the forearm to the hand in the longitudinal direction while taking the angle of the ultrasound probe 2 into account. In other words, the generation function 556 generates a scanning path through which the ultrasound probe 2 vertically moves and the angle thereof changes as the ultrasound probe 2 slides from the forearm to the hand in the longitudinal direction.

The generation function 556 can also generate a scanning path on which ultrasonic wave is transmitted and received to and from the scanning target site at a predetermined angle. In such a case, for example, the generation function 556 detects a position, the distance from which to the ultrasound probe 2 is shortest at the scanning target site, and generates a scanning path on which scanning is executed in a direction at the predetermined angle relative to the detected position. For example, as illustrated in FIG. 7B, the generation function 556 determines the angle of the ultrasound probe so that ultrasonic wave is transmitted and received in a direction orthogonal to Tangent Line L2 at a predetermined angle relative to the forearm. Then, the generation function 556 calculates coordinates, the distances from which to the body surface are equal to "Distance a4" in the longitudinal direction at the determined angle. Then, the generation function 556 connects the calculated coordinates to generate a scanning path.

The angle of the ultrasound probe 2 is set for each scanning target site and each examination content and stored in the memory 54 in advance. The generation function 556 reads this information from the memory 54 when setting the angle of the ultrasound probe 2.

The generation function 556 can also generate a scanning path on which ultrasonic wave is transmitted and received while the angle of the ultrasound probe 2 is changed along a curved face of the scanning target site. In such a case, for example, the generation function 556 calculates an angle perpendicular to a tangent line on a curved line indicating the body surface at a predetermined section of the scanning target site, and generates a scanning path on which ultrasonic wave is transmitted and received in a direction at the calculated angle. For example, as illustrated in FIG. 7C, the generation function 556 sets a tangent line on the body surface from Tangent Line L2 to Tangent Line L3 on a curved line indicating the forearm, and calculates coordinates, the distances from which to the transmission-reception surface of the ultrasound probe 2 are equal to "Distance a4" for each set tangent line along the curved line. Then, the generation function 556 connects the calculated coordinates to generate a scanning path.

In the above-described embodiment, a scanning path is generated by the single provisional scanning. However, the embodiment is not limited thereto. A plurality of times of the provisional scanning may be performed, and a plurality of scanning paths may be generated based on the plurality of times of the provisional scanning. For example, when scanning path is generated for each finger in finger rheumatism diagnosis, the provisional scanning is sometimes performed a plurality of times in the ultrasound probe 2 having a transducer element width of "15 cm" approximately.

In such a case, the mechanical mechanism 7 includes a mechanism unit configured to move the ultrasound probe 2 in a direction orthogonal to Arrow a1 and Arrow a2 illustrated in FIG. 2. The control function 551 and the mechanism control function 554 execute a plurality of times of the provisional scanning of the hand as the scanning target site. For example, the control function 551 and the mechanism control function 554 control the mechanical mechanism 7 to provisionally scan a region on the thumb side of the hand from the start position of the provisional scanning. Then, when the provisional scanning is executed up to the fingertip, the control function 551 and the mechanism control function 554 return the ultrasound probe 2 to the start position of the provisional scanning, and drive, in the direction orthogonal to Arrow a1 and Arrow a2, the mechanism unit configured to move the ultrasound probe 2, thereby moving the ultrasound probe 2 to the little finger side to execute the provisional scanning again.

Accordingly, the ultrasound diagnostic apparatus 1 executes the provisional scanning of the five fingers. Whether the scanning is executed up to the fingertip is determined based on, for example, the ultrasound image data. For example, the mechanism control function 554 determines that the scanning is executed up to the fingertip when information indicating the body surface is lost in ultrasound image data generated by the image generation function 552.

When the provisional scanning of the five fingers is executed as described above, the generation function 556 generates a canning path for each finger. Specifically, the generation function 556 identifies each finger included in the ultrasound image data based on the ultrasound image data at each time collected by the provisional scanning and information of the drive amount of the mechanical mechanism at each time, and generates a scanning path for each identified finger. The generation function 556 may generate scanning paths of the same type for all fingers or may generate a scanning path of a type selected for each finger. For example, the generation function 556 generates scanning paths of the type illustrated in FIG. 7B for all fingers. Alternatively, the generation function 556 selects any of the types in FIGS. 7A to 7C for each finger and generates a scanning path of the selected type.

As described above, the generation function 556 can generate scanning paths of various kinds of types based on the provisional scanning. The generation function 556 stores each scanning path generated in this manner in the memory 54. The generation function 556 sets a moving speed when the ultrasound probe 2 is moved along the scanning path, generates mechanical mechanism control information associated with the set moving speed, and stores the generated mechanical mechanism control information in the memory 54. The moving speed may be optionally set, and may be set in advance or specified by the operator.

The control function 551 and the mechanism control function 554 read a scanning path stored in the memory 54, and execute scanning based on the read scanning path. Specifically, the control function 551 and the mechanism control function 554 read the mechanical mechanism control information and control the ultrasound probe 2 to perform scanning while moving on the scanning path at a moving speed set in the mechanical mechanism control information.

For example, in a case of Scanning Path a5 illustrated in FIG. 6, the mechanism control function 554 controls drive of the first mechanism unit 721 and drive of the second mechanism unit 722 so that the transmission-reception surface of the ultrasound probe 2 passes through coordinates on Scanning Path a5. Specifically, the mechanism control function 554 controls drive of the first mechanism unit 721 to control slide in the direction of Arrow a1, and controls drive of the second mechanism unit 722 to control slide of the third holding unit 713 in the direction of Arrow a2.

For example, in cases of scanning paths of the types illustrated in FIGS. 7A to 7C, the mechanism control function 554 controls drive of the first mechanism unit 721 and the second mechanism unit 722 to control slide in the direction of Arrow a1 and slide in the direction of Arrow a2, and controls drive of the third mechanism unit 723 to control rotation of the fourth holding unit 714. When a plurality of scanning paths are stored as in a case of finger rheumatism, the mechanism control function 554 further controls, in the direction orthogonal to Arrow a1 and Arrow a2, the mechanism unit configured to move the ultrasound probe 2.

While the mechanism unit 72 is controlled by the mechanism control function 554, the control function 551 controls transmission and reception of ultrasonic wave to collect ultrasound image data corresponding to a scanning path.

In the above-described embodiment, a scanning path, the distance from which to the body surface is equal to a predetermined distance is generated. However, the distance from the body surface may be determined based on the focal point of the ultrasound probe 2. Specifically, the generation function 556 calculates a distance by which the ultrasound probe 2 is to be separated from the body surface of the subject based on the focal point of the ultrasound probe 2, and generates a scanning path on which the ultrasound probe 2 is moved while being separated by the calculated distance.

In such a case, the generation function 556 acquires the position of the focal point of the ultrasound probe currently used. Then, the generation function 556 sets the distance between the body surface and the transmission-reception surface so that the acquired position of the focal point coincides with a desired position in the body cavity. For example, when the focal point is positioned at "10 cm" from the transmission-reception surface of the ultrasound probe and the position of the focal point is set to be at "2 cm" inside the body surface, the generation function 556 sets the distance between the body surface and the transmission-reception surface to be "8 cm" and generates a scanning path.

Figure 8:
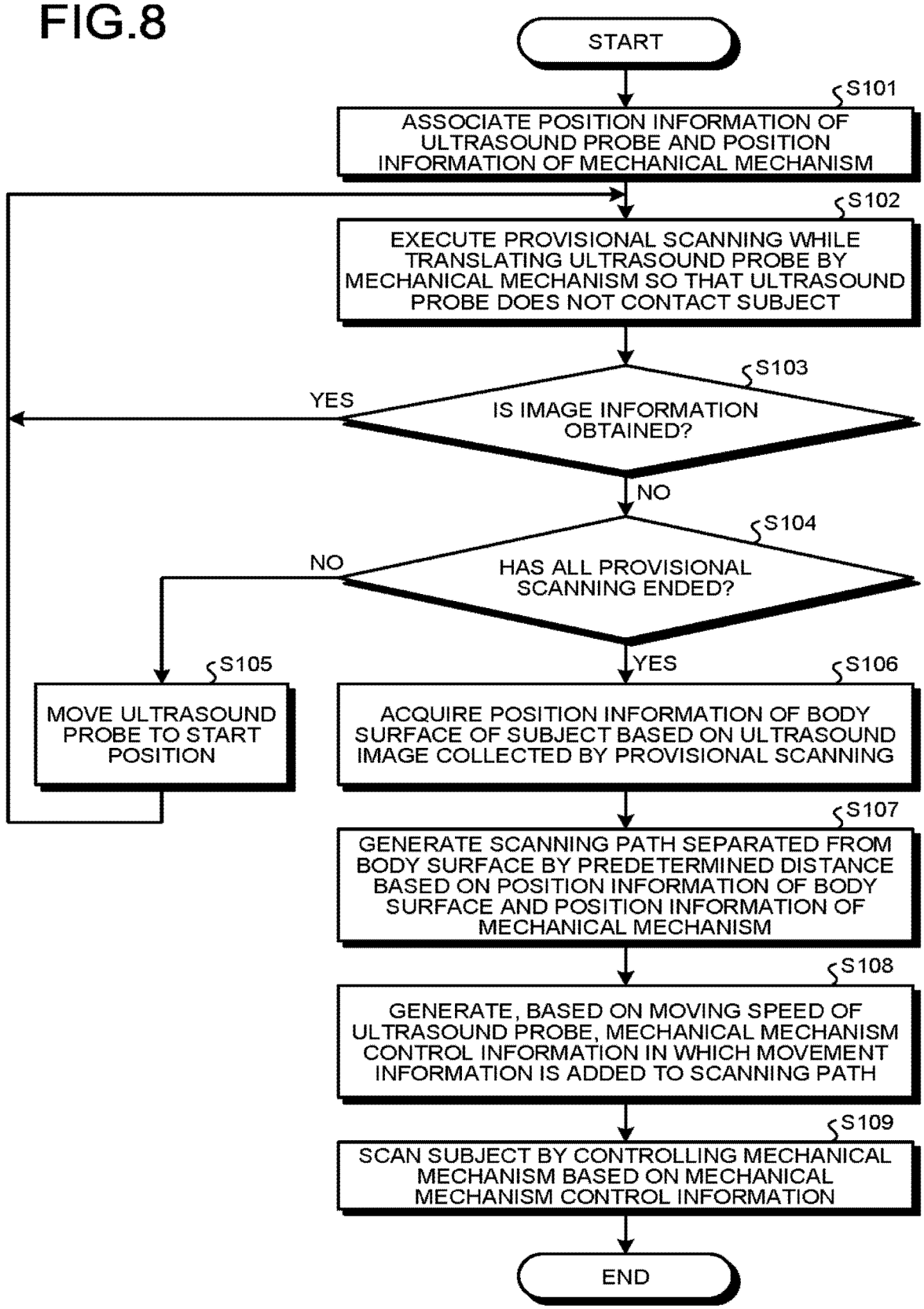
FIG. 8 is a flowchart for describing the procedure of processing by the ultrasound diagnostic apparatus according to the first embodiment.

The following describes processing by the ultrasound diagnostic apparatus 1 according to the first embodiment with reference to FIG. 8. FIG. 8 is a flowchart for describing the procedure of the processing by the ultrasound diagnostic apparatus 1 according to the first embodiment. FIG. 8 illustrates the procedure of the processing when the provisional scanning is executed a plurality of times. Step S101 illustrated in FIG. 8 is executed when the processing circuitry 55 reads a computer program corresponding to the alignment function 555 from the memory 54. Steps S102 to S105 and S109 are executed when the processing circuitry 55 reads computer programs corresponding to the control function 551 and the mechanism control function 554 from the memory 54. Step S106 is executed when the processing circuitry 55 reads a computer program corresponding to the acquisition function 553 from the memory 54. Steps S107 and S108 are executed when the processing circuitry 55 reads a computer program corresponding to the generation function 556 from the memory 54.

In the ultrasound diagnostic apparatus 1 according the first embodiment, the processing circuitry 55 associates the position information of the ultrasound probe 2 and the position information (drive amount information) of the mechanical mechanism 7 (step S101). Then, the processing circuitry 55 executes the provisional scanning while translating the ultrasound probe 2 by the mechanical mechanism 7 so that the ultrasound probe 2 does not contact the subject (step S102), and determines whether image information is obtained (step S103).

When the image information is obtained (positive determination at step S103), the processing circuitry 55 continues the processing at step S102. When the image information is not obtained (negative determination at step S103), the processing circuitry 55 determines whether all provisional scans have ended (step S104). When not all provisional scans have ended (negative determination at step S104), the processing circuitry 55 moves the ultrasound probe to the start position (step S105), and executes the processing at step S102.

When all provisional scans have ended (positive determination at step S104), the processing circuitry 55 acquires position information of the body surface of the subject based on ultrasound images collected by the provisional scanning (step S106), and generates a scanning path separated from the body surface by a predetermined distance based on position information of the body surface and position information of the mechanical mechanism 7 (step S107).

In addition, tree processing circuitry 55 generates, based on the moving speed of the ultrasound probe 2, mechanical mechanism control information in which movement information is added to the scanning path (step S108). Thereafter, the processing circuitry 55 scans the subject by controlling the mechanical mechanism 7 based on the mechanical mechanism control information (step S109).

As described above, according the first embodiment, the ultrasound probe 2 transmits and receives ultrasonic waves. The mechanical mechanism 7 holds and moves the ultrasound probe 2 while the ultrasonic-wave transmission-reception surface of the ultrasound probe 2 is pointed to the subject. The generation function 556 generates, based on information of the positional relation between the ultrasound probe 2 moved by the mechanical mechanism 7 and the subject, a scanning path on which the ultrasound probe is moved when ultrasound scanning is executed on the subject. Thus, the ultrasound diagnostic apparatus 1 according to the first embodiment can generate the scanning path by using the positional relation between the subject and the ultrasound probe, thereby allowing easy generation of the scanning path.

According to the first embodiment, the generation function 556 acquires the distance between the body surface of the subject and the ultrasonic-wave transmission-reception surface of the ultrasound probe based on reflected wave data collected as the ultrasound probe is moved relative to the subject in a non-contact manner by the mechanical mechanism 7, and generates a scanning path based on the acquired distance. Thus, the ultrasound diagnostic apparatus 1 according to the first embodiment can easily acquire the positional relation between the subject and the ultrasound probe 2, thereby allowing easy generation of the scanning path.

According to the first embodiment, the generation function 556 calculates a distance by which the ultrasound probe 2 is to be separated from the body surface of the subject based on the focal point of the ultrasound probe 2, and generates a scanning path on which the ultrasound probe is moved while being separated by the calculated distance. Thus, the ultrasound diagnostic apparatus 1 according to the first embodiment can automatically acquire ultrasound image data with the focal point being set to a desired position, thereby allowing easy generation of an easily observable image.

According to the first embodiment, the generation function 556 additionally generates, based on information of the three-dimensional positional relation between the ultrasound probe 2 moved by the mechanical mechanism 7 and the subject, the angle information of the ultrasound probe 2 when ultrasound scanning is executed on the subject. Thus, the ultrasound diagnostic apparatus 1 according to the first embodiment can acquire ultrasound image data from various angles in accordance with conditions, thereby allowing more stable ultrasound diagnosis.

According to the first embodiment, the mechanical mechanism 7 executes ultrasound scanning on the subject by moving the ultrasound probe 2 based on a scanning path generated by the generation function 556. Thus, the ultrasound diagnostic apparatus 1 according to the first embodiment can stably provide easily observable ultrasound image data when operated by any operator.

Second Embodiment

Figure 9:
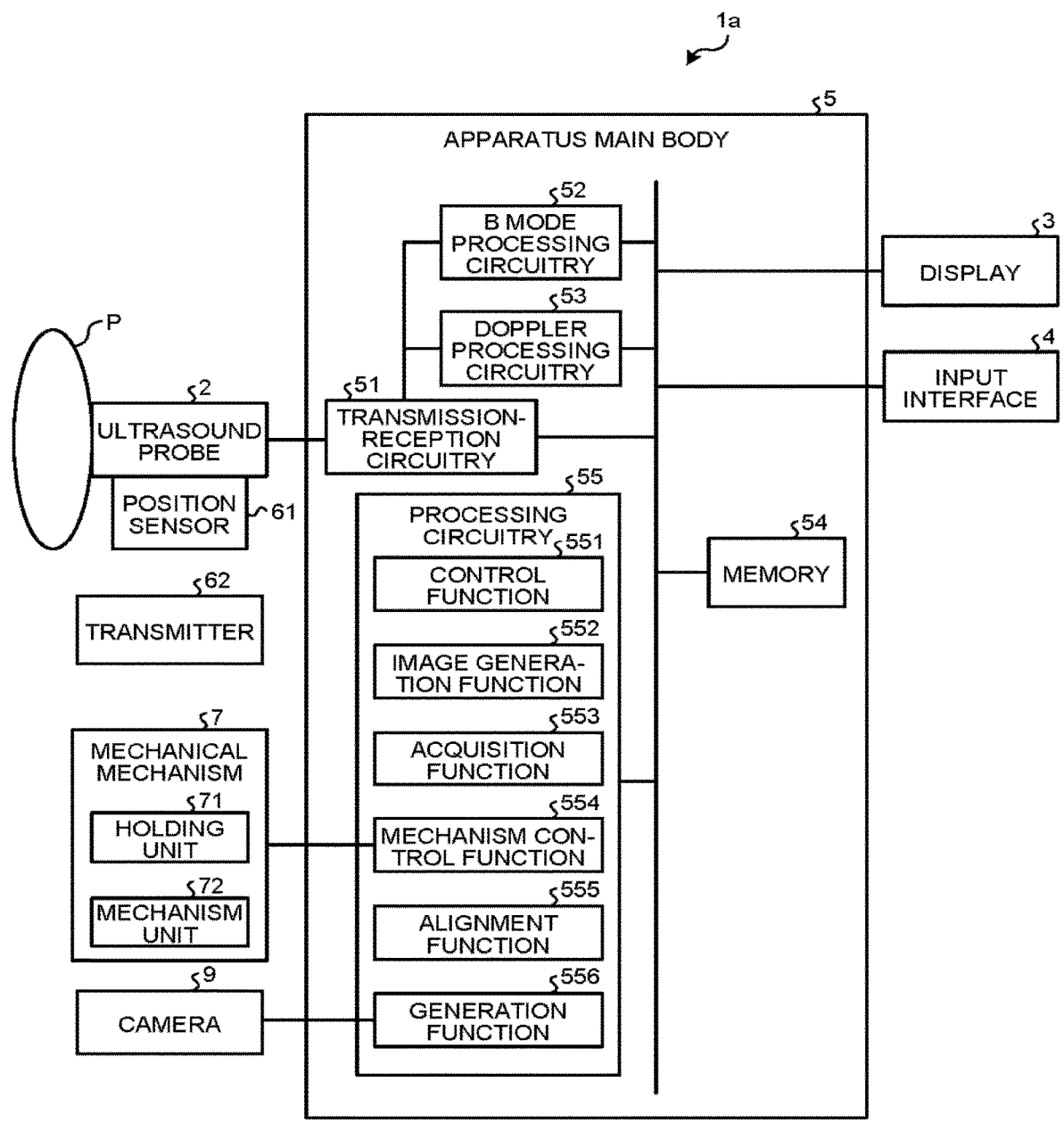
FIG. 9 is a block diagram illustrating an exemplary configuration of an ultrasound diagnostic apparatus according to a second embodiment.

In the first embodiment, the distance between the ultrasound probe 2 and the body surface is calculated from ultrasound image data collected by the provisional scanning. The following description of a second embodiment is made on a case in which the distance between the ultrasound probe 2 and the body surface is calculated by using a video obtained through image capturing of the states of the subject and the ultrasound probe 2 (or the mechanical mechanism 7) with a camera. FIG. 9 is a block diagram illustrating an exemplary configuration of an ultrasound diagnostic apparatus 1a according to the second embodiment. The ultrasound diagnostic apparatus 1a according to the second embodiment is different from the first embodiment in that a camera 9 is connected and the generation function 556 performs different processing. The following description will be made mainly on this difference.

In the ultrasound diagnostic apparatus 1a according to the second embodiment, the camera 9 collects a video illustrating the positional relation between the subject and the ultrasound probe 2 (or the mechanical mechanism 7), and transmits the collected video to the generation function 556. For example, the camera 9 is disposed in a room in which ultrasound diagnosis is performed, and is connected with the ultrasound diagnostic apparatus 1a. Then, under control of the generation function 556, the camera 9 collects a video of scanning of the subject by the mechanical mechanism 7 and transmits the video to the ultrasound diagnostic apparatus 1a.

The video collected by the camera 9 is collected in a direction orthogonal to a section in ultrasound image data. For example, the camera 9 collects a video illustrating the positional relation between the subject and the ultrasound probe 2 (or the mechanical mechanism 7) in the direction illustrated in FIG. 3. In scanning of the subject by the mechanical mechanism 7 when the camera 9 collects a video, ultrasonic wave does not need to be actually transmitted and received. When the positional relation between the subject and the ultrasound probe 2 (or the mechanical mechanism 7) is three-dimensionally collected, the cameras 9 are installed at a plurality of positions to collect a plurality of videos.

The generation function 556 according to the second embodiment acquires the distance between the body surface of the subject and the ultrasonic-wave transmission-reception surface of the ultrasound probe 2 based on an image obtained by capturing a state in which the ultrasound probe 2 is moved relative to the subject in a non-contact manner by the mechanical mechanism 7, and generates a scanning path based on the acquired distance. Specifically, the generation function 556 calculates the distance between the ultrasound probe 2 and the body surface at each position in the mechanical mechanism 7 based on a video acquired from the camera 9, and generates a scanning path based on the calculated distance.

For example, the generation function 556 calculates, from the video, the distance between the body surface and the transmission-reception surface of the ultrasound probe 2 for each time. Then, the generation function 556 calculates, based on the calculated distance, the coordinates of a position separated from the body surface by a predetermined distance for each position of the ultrasound probe 2. Then, the generation function 556 connects the calculated coordinates to generate a scanning path.

When the ultrasound probe 2 is included in the video received from the camera 9, the generation function 556 calculates the distance between the subject and the transmission-reception surface of the ultrasound probe 2 directly from the video. When the ultrasound probe 2 is not included in the video but only the mechanical mechanism 7 is included, the generation function 556 calculates the distance between the subject and the transmission-reception surface of the ultrasound probe 2 from the video based on the positional relation of the ultrasound probe 2 relative to the mechanical mechanism 7. In other words, the generation function 556 calculates the position of the transmission-reception surface of the ultrasound probe 2 held by the mechanical mechanism 7 from the structure of the mechanical mechanism 7.

Figure 10:
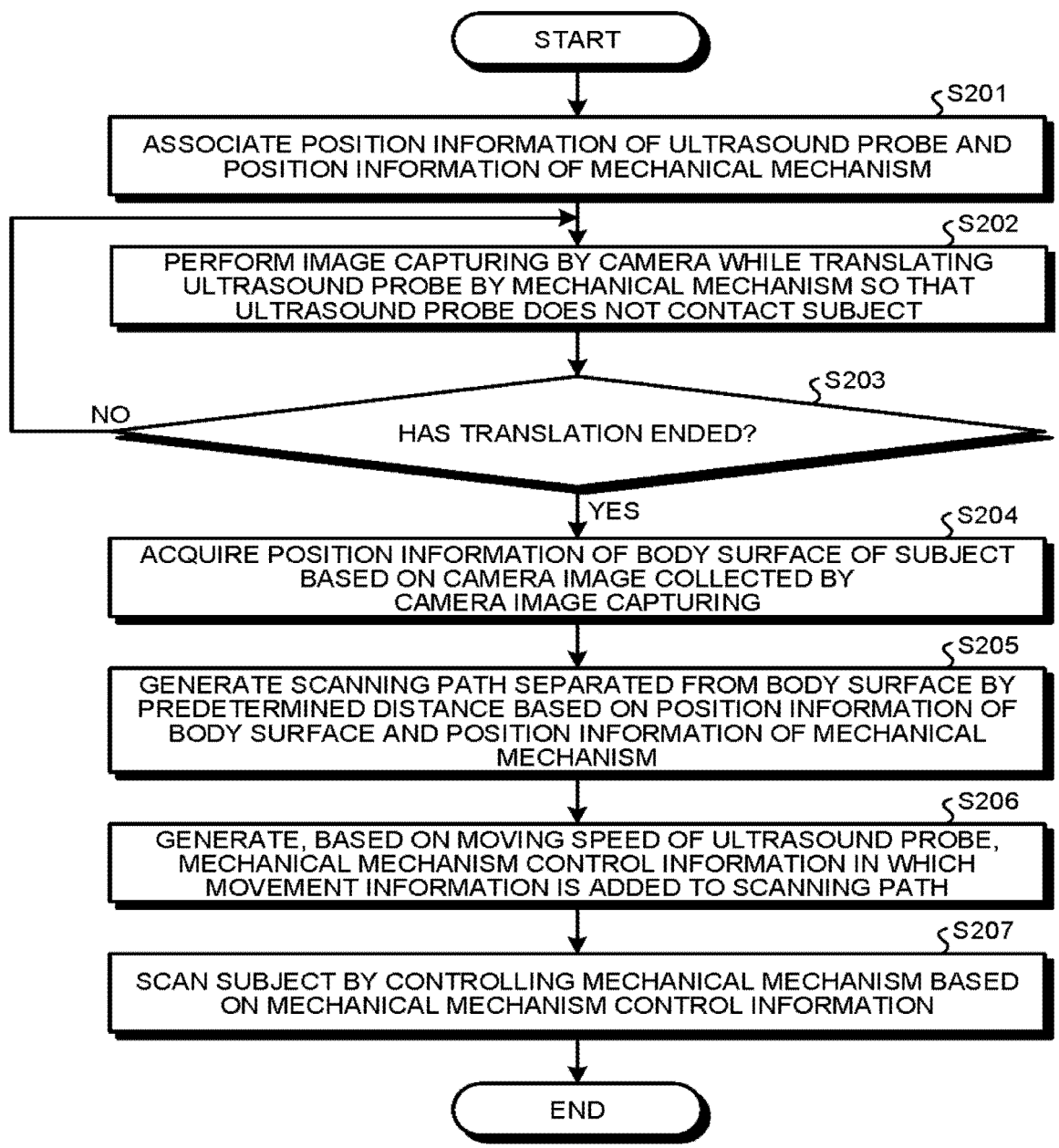
FIG. 10 is a flowchart for describing the procedure of processing by the ultrasound diagnostic apparatus according to the second embodiment.

The following describes processing by the ultrasound diagnostic apparatus 1a according to the second embodiment with reference to FIG. 10. FIG. 10 is a flowchart for describing the procedure of the processing by the ultrasound diagnostic apparatus 1a according to the second embodiment. Step S201 illustrated in FIG. 10 is executed when the processing circuitry 55 reads a computer program corresponding to the alignment function 555 from the memory 54. Steps S202 and S203 are executed when the processing circuitry 55 reads computer programs corresponding to the mechanism control function 554 and the generation function 556 from the memory 54. Step S204 executed when the processing circuitry 55 reads a computer program corresponding to the acquisition function 553 from the memory 54. Steps S205 and S206 are executed when the processing circuitry 55 reads a computer program corresponding to the generation function 556 from the memory 54. Step S207 is executed when the processing circuitry 55 reads computer programs corresponding to the control function 551 and the mechanism control function 554 from the memory 54.

In the ultrasound diagnostic apparatus 1a according to the second embodiment, the processing circuitry 55 associates the position information of the ultrasound probe 2 and the position information (drive amount information) of the mechanical mechanism 7 (step S201). Then, the processing circuitry 55 performs image capturing by the camera 9 while translating the ultrasound probe 2 by the mechanical mechanism 7 so that the ultrasound probe 2 does not contact the subject (step S202), and determines whether the translation has ended (step S203).

When the translation has not ended (negative determination at step S203), the processing circuitry 55 continues the processing at step S202. When the translation has ended (positive determination at step S203), the processing circuitry 55 acquires position information of the body surface of the subject based on a camera image collected by camera image capturing (step S264), and calculates the distance between the ultrasound probe 2 and the body surface.

Then, the processing circuitry 55 generates a scanning path separated from the body surface by a predetermined distance based on the distance between the ultrasound probe and the body surface and position information of the mechanical mechanism 7 (drive amount information) (step S205).

In addition, the processing circuitry 55 generates, based the moving speed of the ultrasound probe 2, mechanical mechanism control information in which movement information is added to the scanning path (step S206).

Thereafter, the processing circuitry 55 scans the subject by controlling the mechanical mechanism 7 based on the mechanical mechanism control information (step S207).

As described above, according to the second embodiment, the generation function 556 acquires the distance between the body surface of the subject and the ultrasonic-wave transmission-reception surface of the ultrasound probe based on an image obtained by capturing a state in which the ultrasound probe 2 is moved relative to the subject in a non-contact manner by the mechanical mechanism 7, and generates a scanning path based on the acquired distance. Thus, the ultrasound diagnostic apparatus 1a according to the second embodiment can easily acquire the positional relation between the subject and the ultrasound probe 2, thereby allowing easy generation of the scanning path.

Third Embodiment

Figure 11:
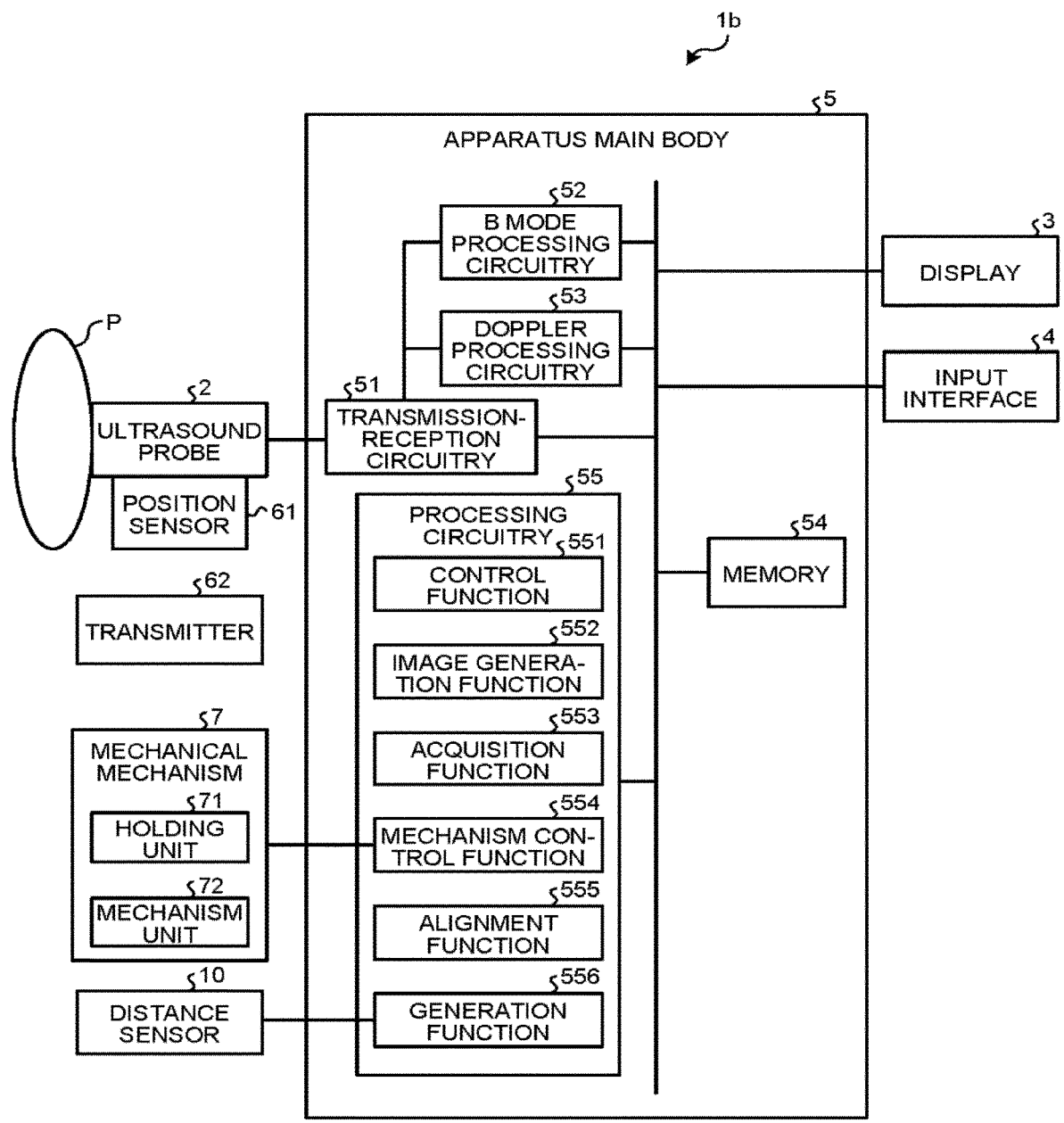
FIG. 11 is a block diagram illustrating an exemplar configuration of an ultrasound diagnostic apparatus according to a third embodiment.

In the first embodiment, the distance between the ultrasound probe 2 and the body surface is calculated from ultrasound image data collected by the provisional scanning. The following description of a third embodiment is made on a case in which the distance between the subject and the ultrasound probe 2 (or the mechanical mechanism 7) is measured by a distance sensor. FIG. 11 is a block diagram illustrating an exemplary configuration of the ultrasound diagnostic apparatus 1 according to the third embodiment. The ultrasound diagnostic apparatus 1 according to the third embodiment is different from the first embodiment in that a distance sensor 10 is connected and the generation function 556 performs different processing. The following description will be made mainly on this difference.

In an ultrasound diagnostic apparatus 1b according to the third embodiment, the distance sensor 10 measures the distance between the subject and the ultrasound probe 2 or the mechanical mechanism 7), and transmits the measured distance to the generation function 556. For example, the distance sensor 10 is a laser distance measurement device mounted at a predetermined position on the ultrasound probe 2 or at a predetermined position on the mechanical mechanism 7 and connected with the ultrasound diagnostic apparatus 1b. Under control of the generation function 556, the distance censor 10 measures the distance to the body surface of the subject each time the subject is scanned by the mechanical mechanism 7, and transmits the result of the measurement to the ultrasound diagnostic apparatus 1b. Ultrasonic wave does not need to be actually transmitted and received in the scanning of the subject by the mechanical mechanism 7 when the distance sensor measures the distance.

The generation function 556 according to the third embodiment acquires the distance between the body surface of the subject and the ultrasonic-wave transmission-reception surface of the ultrasound probe 2 based on the distance information acquired by the distance sensor 10 while the ultrasound probe 2 is moved relative to the subject in a non-contact manner by the mechanical mechanism 7, and generates a scanning path based on the acquired distance.

For example, the generation function 556 calculates the coordinates of a position separated from the body surface by a predetermined distance for each position of the ultrasound probe 2 based on the distance at each time. Then, the generation function 556 connects the calculated coordinates to generate a scanning path.

The generation function 556 calculates the distance between the subject and the transmission-reception surface of the ultrasound probe 2 from the distance information acquired by the distance sensor 10 based on the positional relation (information of a position at which the distance sensor 10 is attached) of the distance sensor 10 with the mechanical mechanism 7 or the ultrasound probe 2. When the positional relation between the subject and the ultrasound probe 2 (or the mechanical mechanism 7) is three-dimensionally collected, the distance sensors 10 are mounted at a plurality of positions to acquire a plurality of pieces of distance information.

Figure 12:
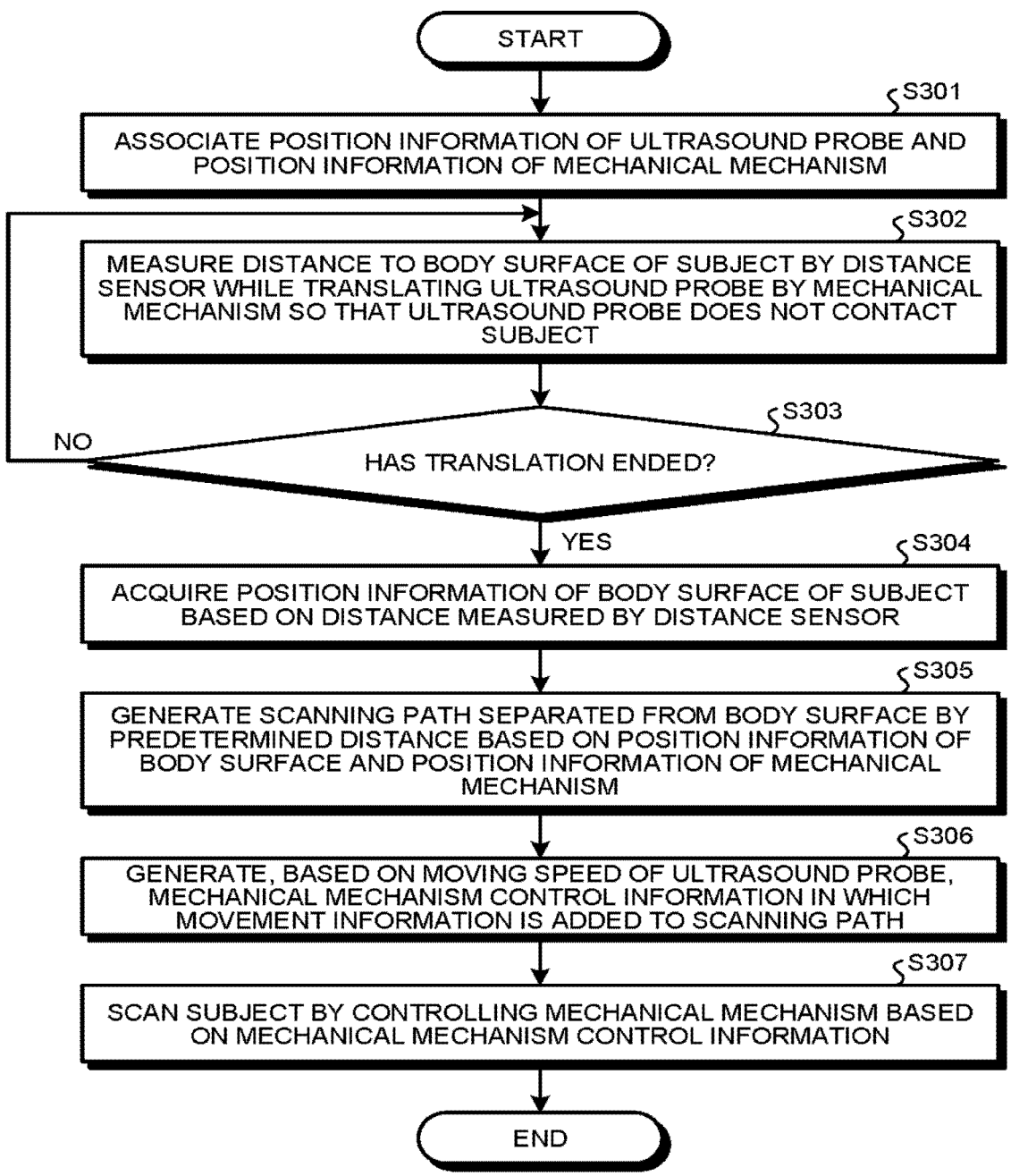
FIG. 12 is a flowchart for describing the procedure of processing by the ultrasound diagnostic apparatus according to the third embodiment.

The following describes processing by the ultrasound diagnostic apparatus 1b according to the third embodiment with reference to FIG. 12. FIG. 12 is a flowchart for describing the procedure of the processing by the ultrasound diagnostic apparatus 1b according to the third embodiment. Step S301 illustrated in FIG. 12 is executed when the processing circuitry 55 reads a computer program corresponding to the alignment function 555 from the memory 54. Steps S302 and S303 are executed when the processing circuitry 55 reads computer programs corresponding to the mechanism control function 554 and the generation function 556 from the memory 54. Steps S304 to S306 are executed when the processing circuitry 55 reads a computer program corresponding to the generation function 556 from the memory 54. Step S307 is executed when the processing circuitry 55 reads computer programs corresponding to the control function 551 and the mechanism control function 554 from the memory 54.

In the ultrasound diagnostic apparatus 1b according to the third embodiment, the processing circuitry 55 associates the position information of the ultrasound probe 2 and the position information (drive amount information) of the mechanical mechanism 7 (step S301). Then, the processing circuitry 55 measures the distance to the body surface of the subject by the distance sensor 10 while translating the ultrasound probe 2 by the mechanical mechanism 7 so that the ultrasound probe 2 does not contact the subject (step S302), and determines whether the translation has ended (step S303).

When the translation has not ended (negative determination at step S303), the processing circuitry 55 continues the processing at step S302. When the translation has ended (positive determination at step S303), the processing circuitry 55 acquires position information of the body surface of the subject based on the distance information measured by the distance sensor 10 (step S304), and calculates the distance between the ultrasound probe 2 and the body surface.

Then, the processing circuitry 55 generates a scanning path separated from the body surface by a predetermined distance based on the distance between the ultrasound probe and the body surface and position information of the mechanical mechanists 7 (drive amount information) (step S305).

In addition, the processing circuitry 55 generates, based on the moving speed of the ultrasound probe 2, the mechanical mechanism control information in which movement information is added to the scanning path (step S306). Thereafter, the processing circuitry 55 scans the subject by controlling the mechanical mechanism 7 based on the mechanical mechanism control information (step S307).

As described above, according to the third embodiment, the generation function 556 acquires the distance between the body surface of the subject and the ultrasonic-wave transmission-reception surface of the ultrasound probe 2 based on the distance information acquired by the distance sensor 10 while the ultrasound probe 2 is moved relative to the subject in a non-contact manner by the mechanical mechanism 7, and generates a scanning path based on the acquired distance. Thus, the ultrasound diagnostic apparatus 1b according to the third embodiment can easily acquire the positional relation between the subject and the ultrasound probe 2, thereby allowing easy generation of the scanning path.

Fourth Embodiment

Figure 13:
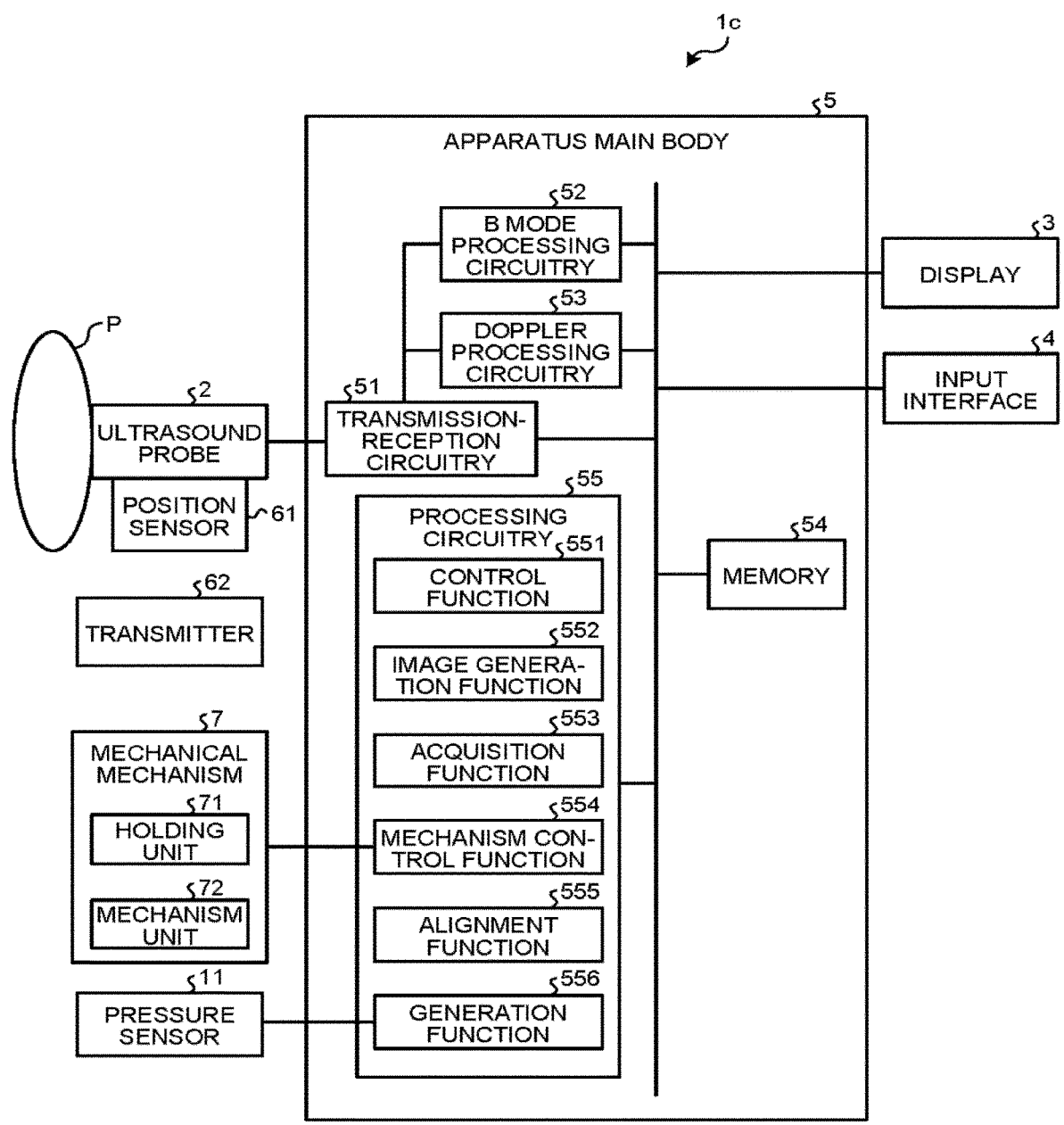
FIG. 13 is a block diagram illustrating an exemplary configuration of an ultrasound diagnostic apparatus according to a fourth embodiment.

In the first to third embodiments, scanning is executed relative to the subject in a non-contact manner. The following description of a fourth embodiment is made on a case in which scanning is executed in contact with the subject to generate a scanning path. FIG. 13 is a block diagram illustrating an exemplary configuration of an ultrasound diagnostic apparatus 1c according to the fourth embodiment. The ultrasound diagnostic apparatus is according to the fourth embodiment is different from the first embodiment in that a pressure sensor 11 is connected and the generation function 556 performs different processing. The following description will be made mainly on this difference.

In the ultrasound diagnostic apparatus 1c according to the fourth embodiment, the pressure sensor 11 measures pressure applied between the subject and the transmission-reception surface of the ultrasound probe 2, and transmits the measured pressure to the generation function 556. For example, the pressure sensor 11 is disposed at a predetermined position on the transmission-reception surface of the ultrasound probe 2 and connected with the ultrasound diagnostic apparatus 1c. Then, under control of the generation function 556, the pressure sensor 11 continuously measures pressure while the subject is scanned by the mechanical mechanism 7, and transmits the result of the measurement to the generation function 556. When movement by the mechanical mechanism 7 is performed while the ultrasound probe 2 is in contact with the subject, for example, thickly applied gel or a resin plate having a low-acoustic attenuation characteristic is used as an acoustic medium.

The generation function 556 according to the fourth embodiment generates a scanning path based on pressure applied between the subject and the ultrasound probe while the ultrasound probe 2 is moved relative to the subject in a contact manner by the mechanical mechanism 7. For example, the generation function 556 generates, as a scanning path, a locus when the ultrasound probe 2 is moved so that the pressure acquired by the pressure sensor 11 has a predetermined value.

Specifically, the generation function 556 compares the value of the pressure acquired at each time with a predetermined value, calculates coordinates converted from the coordinates of the transmission-reception surface of the ultrasound probe 2 at each time based on a result of the comparison, and connects the calculated coordinates to generate a scanning path. For example, when the pressure value at time t1 is higher than a predetermined value, the generation function 556 acquires coordinates to which the coordinates of the transmission-reception surface of the ultrasound probe 2 at time t1 are moved in the direction departing from the body surface. The generation function 556 determines the moving amount of the coordinates based on information associating a pressure value and a moving amount and stored in the memory 54 in advance. When the value measured by the pressure sensor 11 is equal to the predetermined value, the current coordinates of the transmission-reception surface of the ultrasound probe 2 are included in a scanning path. The generation function 556 generates a scanning path by executing the above-described processing for each time when the pressure is measured, and stores the generated scanning path in the memory 54. For example, the scanning path stored in the memory 54 is managed for each subject, and read and used when the subject is subjected to ultrasound scanning next time.

When the positional relation between the subject and the ultrasound probe 2 is three-dimensionally collected, the pressure sensors 11 are mounted at a plurality of positions to acquire a plurality of pieces of pressure information. For example, when a scanning path to which angle information is added is to be generated, the generation function 556 sets, as predetermined values to the pressure sensors 11 disposed at a plurality of positions, values of the pressure sensors when the ultrasound probe 2 has a desired angle. Then, the generation function 556 executes the above-described processing while comparing the result of measurement by the pressure sensor 11 at each position with the predetermined value set to the pressure sensor, thereby generating a scanning path to which angle information is added.

Position control can be performed in real time while the ultrasound probe 2 is moved by the mechanical mechanism 7 by transmitting the coordinates (coordinates after conversion based on the pressure value) calculated by the generation function 556 to the mechanism control function 554. Specifically, the control function 551 executes ultrasound scanning while the mechanism control function 554 controls the transmission-reception surface of the ultrasound probe to move to the coordinates received from the generation function 556.

In the above-described embodiment, the pressure sensor 11 is used to detect the contact state of the ultrasound probe 2 relative to the subject. However, the embodiment is not limited thereto, and an elasticity value acquired by elastography may be used in place of the pressure sensor 11. In such a case, the generation function 556 generates, as a scanning path, a locus when the ultrasound probe 2 is moved so that the elasticity value acquired by elastography is equal to a predetermined value.

In the above-described embodiment, control is performed so that the pressure or the elasticity value is equal to a predetermined value. However, the embodiment is not limited thereto, and for example, control may be performed so that the pressure or the elasticity value is in a predetermined range or equal to or lower than a predetermined threshold.

Figure 14:
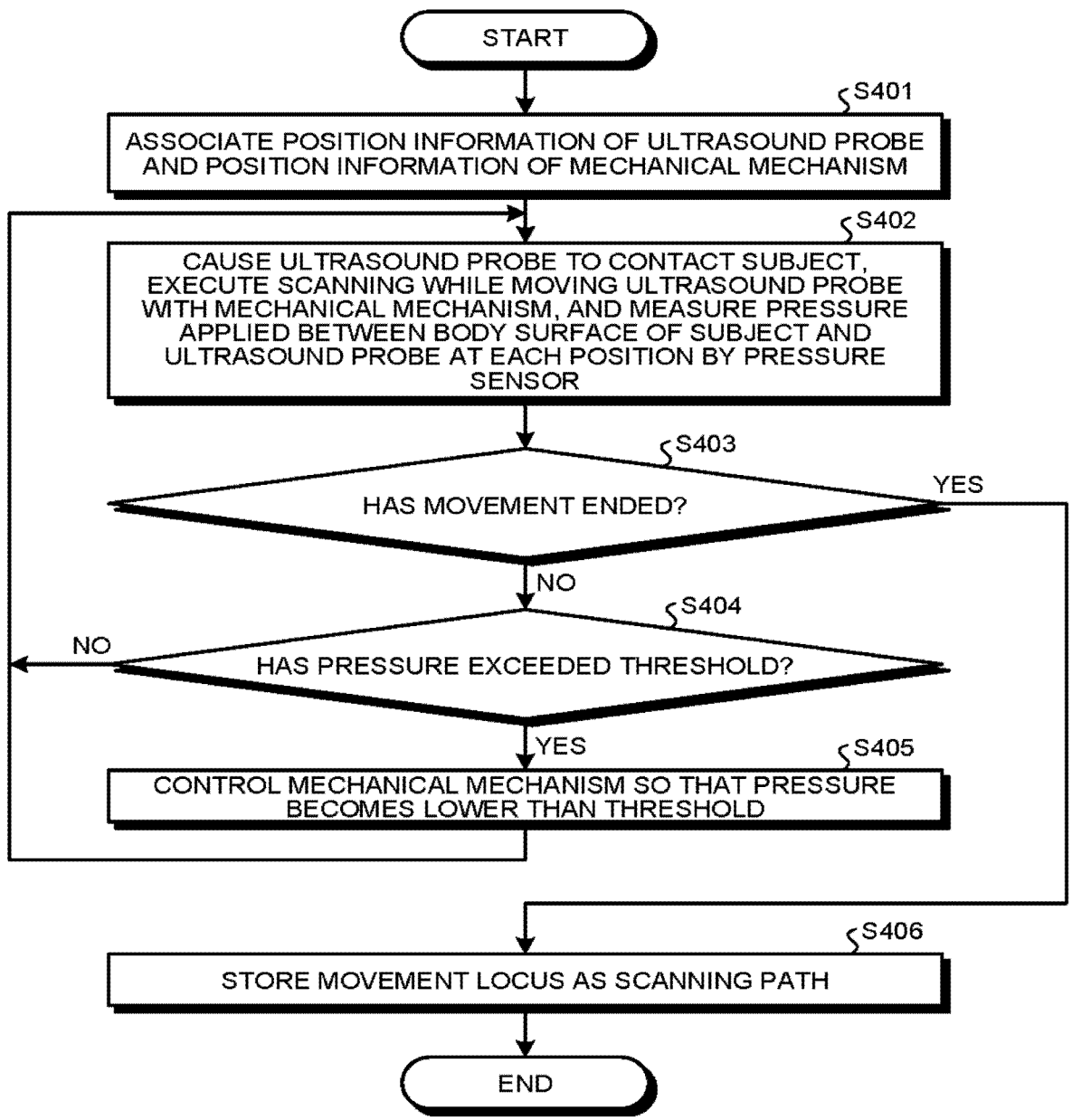
FIG. 14 is a flowchart for describing the procedure of processing by the ultrasound diagnostic apparatus according to the fourth embodiment.

The following describe processing by the ultrasound diagnostic apparatus 1c according to the fourth embodiment with reference to FIG. 14. FIG. 14 is a flowchart for describing the procedure of the processing by the ultrasound diagnostic apparatus 1c according to the fourth embodiment. In the case of FIG. 14, control is performed so that pressure does not exceed a threshold. Step S401 illustrated in FIG. 14 is executed when the processing circuitry 55 reads a computer program corresponding to the alignment function 555 from the memory 54. Steps S402 to S404 are executed when the processing circuitry 55 reads computer programs corresponding to the mechanism control function 554 and the generation function 556 from the memory 54. Step S405 is executed when the processing circuitry 55 reads a computer program corresponding to the mechanism control function 554 from the memory 54. Step S406 is executed when the processing circuitry 55 reads a computer program corresponding to the generation function 556 from the memory 54.

In the ultrasound diagnostic apparatus 1c according to the fourth embodiment, the processing circuitry 55 associates the position information of the ultrasound probe 2 and the position information (drive amount information) of the mechanical mechanism 7 (step S401). Then, the processing circuitry 55 causes the ultrasound probe 2 to contact the subject and executes scanning while the ultrasound probe is moved by the mechanical mechanism 7, measures the pressure applied between the body surface of the subject and the ultrasound probe 2 at each position by the pressure sensor 11 (step S402), and determines whether the movement has ended (step S403).

When the movement has not ended (negative determination at step S403), the processing circuitry 55 determines whether the pressure has exceeded the threshold (step S404). When the pressure has exceeded the threshold (positive determination at step S404), the processing circuitry 55 controls the mechanism 7 so that the pressure becomes lower than the threshold (step S405). When the pressure has not exceeded the threshold (negative determination at step S404), the processing circuitry 55 continues the processing at step S402.

When the movement has ended at step S403 (positive determination at step S403), the processing circuitry 55 stores the locus of the movement as a scanning path (step S406).

As described above, according to the fourth embodiment, the generation function 556 generates a scanning path based on the pressure applied between the subject and the ultrasound probe 2 while the ultrasound probe 2 is moved relative to the subject in a contact manner by the mechanical mechanism 7. Thus, the ultrasound diagnostic apparatus 1c according to the fourth embodiment can generate a scanning path simultaneously with automatic execution of scanning by the mechanical mechanism 7, thereby performing fast ultrasound diagnosis and allowing easy generation of a scanning path used in the subsequent scanning.

Fifth Embodiment

In the first to fourth embodiments, the positional relation between the body surface of the subject and the transmission-reception surface of the ultrasound probe 2 is acquired by using a single means (for example, reflected wave data acquired by provisional scanning or an image captured by a camera), and a scanning path is generated based on the acquired positional relation. In a fifth embodiment, a plurality of pieces of information of the positional relation between the body surface of the subject and the transmission-reception surface of the ultrasound probe 2 are acquired by using a plurality of means, and a scanning path is generated based on the acquired pieces of information of the positional relation.

An ultrasound diagnostic apparatus according to the fifth embodiment has a configuration in accordance with each means configured to acquire information of the positional relation between the body surface of the subject and the transmission-reception surface of the ultrasound probe 2. For example, the ultrasound diagnostic apparatus having the configuration illustrated in FIG. 9 executes each processing described in the first and second embodiments when information of the positional relation between the body surface and the transmission-reception surface of the ultrasound probe 2 is acquired by using reflected wave data acquired by provisional scanning and an image captured by a camera. Specifically, the ultrasound diagnostic apparatus according to the fifth embodiment includes a component of the ultrasound diagnostic apparatus described in the first to fourth embodiments, which is necessary for acquiring information of the positional relation between the body surface of the subject and the transmission-reception surface of the ultrasound probe 2, and executes the corresponding processing.

The following exemplarily describes processing by the ultrasound diagnostic apparatus when information of the positional relation (distance information) between the body surface and the transmission-reception surface of the ultrasound probe 2 is acquired by using reflected wave data acquired by provisional scanning and an image captured by a camera. The following description is merely exemplary, and combination of means for acquiring information of the positional relation between the body surface and the transmission-reception surface of the ultrasound probe 2 is optional. Although the following exemplarily describes a case in which two kinds of means are used as the means for acquiring information of the positional relation between the body surface and the transmission-reception surface of the ultrasound probe 2, the ultrasound diagnostic apparatus may use three or more kinds of means.

For example, when information of the positional relation between the body surface and the transmission-reception surface of the ultrasound probe 2 is acquired by using reflected wave data acquired by provisional scanning and an image captured by a camera, the ultrasound diagnostic apparatus executes each processing described in the first embodiment to execute the provisional scanning, acquires the reflected wave data, and acquires the distance between the body surface and the transmission-reception surface of the ultrasound probe 2 based on the acquired reflected wave data. In addition, the ultrasound diagnostic apparatus executes each processing described in the second embodiment to capture an image by the camera and acquires the distance between the body surface and the transmission-reception surface of the ultrasound probe 2 based on the captured image. The acquisition of the reflected wave data and the image capturing by the camera may be performed simultaneously or may be performed separately.

As described above, when information of the positional relation (distance) between the body surface and the transmission-reception surface of the ultrasound probe 2 has been acquired by each means, the generation function 556 according to the fifth embodiment generates a scanning path based on the distance acquired by each means. The generation function 556 executes scanning path generation in accordance with an operation by the operator and scanning path generation based on comparison between the distance acquired by each means and a threshold. The following sequentially describes the scanning path generation in accordance with an operation by the operator, and the scanning path generation based on comparison between the distance acquired by each means and the threshold.

For example, when a scanning path is to be generated in accordance with an operation by the operator, first, the control function 551 controls the display 3 to display the processing result. Specifically, the control function 551 controls the display 3 to display information related to the distance acquired by each means. For example, the generation function 556 generates a scanning path in accordance with the distance based on the reflected wave data, and a scanning path in accordance with the distance based on the image. The control function 551 controls the display 3 to display the scanning path generated by the generation function 556.

Figure 15:
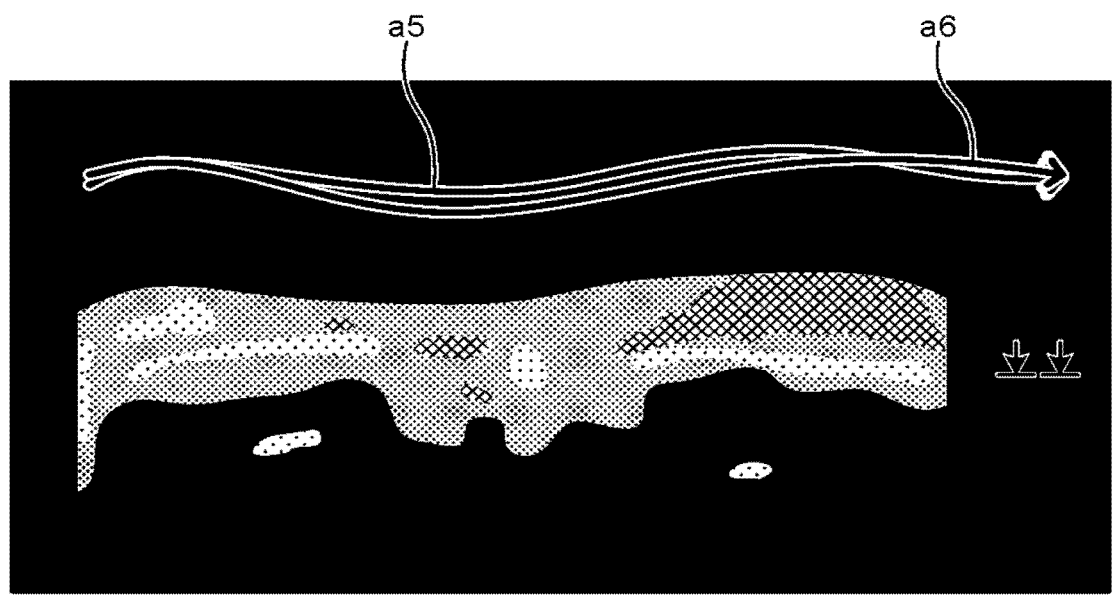
FIG. 15 is a diagram illustrating an exemplary display of the scanning path according to a fifth embodiment.

FIG. 15 is a diagram illustrating exemplary scanning path display according to the fifth embodiment. For example, as illustrated in FIG. 15, the control function 551 controls the display 3 to display Scanning Path a5 in accordance with the distance based on the reflected wave data, and Scanning Path a6 in accordance with the distance based on the image.

The operator refers to the scanning paths displayed on the display 3, and determines a scanning path used to actually move the ultrasound probe 2. For example, the operator operates the input interface 4 to select Scanning Path a5 or Scanning Path a6, thereby determining one of the scanning paths as the scanning path to be used to actually move the ultrasound probe 2.

The control function 551 may compare the distance at each position with a threshold for each scanning path, and change the display form of the scanning path based on the result of the comparison. For example, the control function 551 displays, in an enhanced manner, a position at which the distance between the body surface and the transmission-reception surface of the ultrasound probe 2 exceeds the threshold on Scanning Path a5 and Scanning Path a6 illustrated in FIG. 15. The threshold is used to determine whether the distance acquired by each means is appropriate as the distance between the body surface and the transmission-reception surface of the ultrasound probe 2, and is set in advance. Accordingly, the operator can determine, at glance, whether each scanning path displayed on the display 3 is appropriate.

For example, when no position is enhanced on a scanning path displayed on the display 3, the operator can determine that the scanning path is appropriate in the entire range, and can determine the displayed scanning path as the scanning path to be used to actually move the ultrasound probe 2. For example, when no enhancement is displayed on Scanning Path a5 or Scanning Path a6 illustrated in FIG. 15, the operator can select any of the scanning paths as the scanning path to be used to actually move the ultrasound probe 2.

When a position is displayed in an enhanced manner on a scanning path displayed on the display 3, the operator can determine that the position displayed in an enhancement manner on the scanning path is not appropriate, and can determine a scanning path based on the determination result. For example, when no position is displayed in an enhanced manner on Scanning Path a5 but a position is displayed in an enhanced manner on Scanning Path a6, the operator can select Scanning Path a5 as the scanning path used to actually move the ultrasound probe 2.

For example, when no position is displayed in an enhanced manner on Scanning Path a5 but a position is displayed in an enhanced manner on Scanning Path a6, the operator can partially correct Scanning Path a6 by replacing the distance at the position displayed in an enhanced manner on Scanning Path a6 with the value of the distance at an identical position on Scanning Path a5, and can select Scanning Path a6 as the scanning path to be used to actually move the ultrasound probe 2.

The operator performs the above-described scanning path selection by operating the input interface. The generation function 556 generates, in accordance with the operation by the operator, the scanning path to be used to actually move the ultrasound probe 2 from pieces of distance information acquired by a plurality of means.

Subsequently, when a scanning path is to be generated based on comparison between the distance acquired by each means and a threshold, the generation function 556 compares the distance at each position acquired by each means with the threshold, and determines a scanning path in accordance with the result of the comparison. For example, the generation function 556 compares the distance at each position based on the reflected wave data with the threshold, and extracts a position at which the threshold is exceeded. Similarly, the generation function 556 compares the distance at each position based on the image with the threshold, and extracts a position at which the threshold is exceeded.

When no position at which the threshold is exceeded is extracted in any extraction result, the generation function 556 generates a scanning path based on one of the distances as the scanning path used to actually move the ultrasound probe 2. The generation function 556 may select distance information used for the scanning path generation based on a priority set in advance.

Alternatively, for example, when no position at which the threshold is exceeded is extracted in any extraction result, the generation function 556 may calculate an average value of the distances acquired by the means at each position, and generate a scanning path by using the calculated average value at each position.

When a position at which the threshold is exceeded is extracted, the generation function 556 performs control not to use, for scanning path generation, the value of the distance at which the threshold is exceeded. For example, when a position at which the threshold is exceeded is extracted in only one of the extraction results, the generation function 556 can generate a scanning path by using the distance information when no position at which the threshold is exceeded is extracted. For example, when a position at which the threshold is exceeded is extracted in the result of comparison of the distance at each position based on the reflected wave data with the threshold but no position at which the threshold is exceeded is extracted in the result of comparison of the distance at each position based on the image with the threshold, the generation function 556 generates a scanning path by using the distance at each position based on the image.

When a position at which the threshold is exceeded is extracted, the generation function 556 can partially correct the distance by replacing the value of the distance at the position at which the threshold is exceeded in one of the extraction results with the value of the distance at an identical position at which the threshold is not exceeded in the other extraction result, and can generate a scanning path based on the corrected distance. For example, when a position at which the threshold is exceeded is extracted in the result of comparison of the distance at each position based on the reflected wave data with the threshold but no position at which the threshold is exceeded is extracted in the result of comparison of the distance at each position based on the image with the threshold, the generation function 556 replaces the value of the distance based on the reflected wave data at the position at which the threshold is exceeded with the value of the distance based on the image at an identical position. Then, the generation function 556 generates a scanning path based on the distance based on the reflected wave data, which is partially replaced with the distance based on the image.

When a position at which the threshold is exceeded is extracted, the generation function 556 can correct the distance information by executing linear interpolation by using values at positions adjacent to the position at which the threshold is exceeded, and can generate a scanning path by using the corrected distance. For example, when a position at which the threshold is exceeded is extracted in the result of comparison of the distance at each position based on the reflected wave data with the threshold and a position at which the threshold is exceeded is extracted in the result of comparison of the distance at each position based on the image with the threshold, the generation function 556 first determines that the distance based on the reflected wave data is used to generate a scanning path.

Then, the generation function 556 corrects the value of the distance based on the reflected wave data at the position at which the threshold is exceeded through linear interpolation using values at adjacent positions where the threshold is not exceeded, and generates a scanning path by using the corrected distance.

The above-described example is merely exemplary. Specifically, the generation function 556 may generate a scanning path by combining the above-described processes as appropriate.

Figure 16:
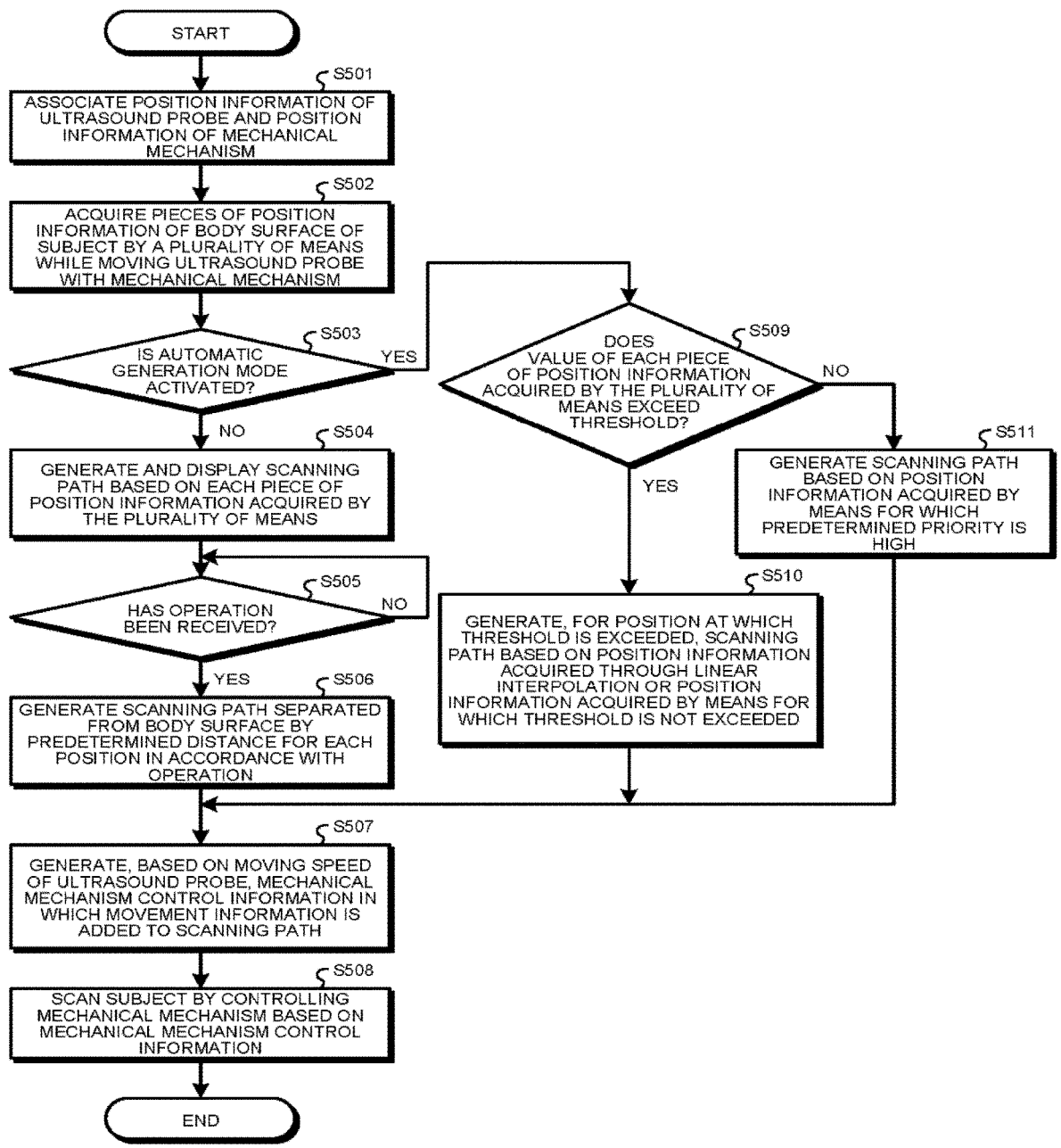
FIG. 16 is a flowchart for describing the procedure of processing by an ultrasound diagnostic apparatus according to the fifth embodiment.

The following describes processing by the ultrasound diagnostic apparatus according to the fifth embodiment with reference to FIG. 16. FIG. 16 is a flowchart for describing the procedure of the processing by the ultrasound diagnostic apparatus according to the fifth embodiment. Step S501 illustrated in FIG. 16 is executed when the processing circuitry 55 reads a computer program corresponding to the alignment function 555 from the memory 54. Steps S502 to S505 and S509 are executed when the processing circuitry 55 reads computer programs corresponding to the control function 551 and the mechanism control function 554 from the memory 54. Steps S506, S507, and S509 to S511 are executed when the processing circuitry 55 reads a computer program corresponding to the generation function 556 from the memory 54.

In the ultrasound diagnostic apparatus according to the fifth embodiment, the processing circuitry 55 associates the position information of the ultrasound probe 2 and the position information (drive amount information) of the mechanical mechanism 7 (step S501). Then, the processing circuitry 55 acquires pieces of position information of the body surface of the subject by a plurality of means while the ultrasound probe 2 is moved by the mechanical mechanism 7 step S502), and determines whether an automatic generation mode is activated (step S503).

When the automatic generation mode is not activated (when an operation by the operator is to be received) (negative determination at step S503), the processing circuitry 55 generates and displays a scanning path based on each of the pieces of position information acquired by the plurality of means (step S504). Then, the processing circuitry 55 determines whether an operation has been received (step S505). When an operation has been received (positive determination at step S505), the processing circuitry 55 generates a scanning path separated from the body surface by a predetermined distance for each position in accordance with the operation (step S506). The processing circuitry 55 waits until an operation is received (negative determination at step S505).

Subsequently, the processing circuitry 55 generates, based on the moving speed of the ultrasound probe 2, the mechanical mechanism control information in which movement information is added to the scanning path (step S507). Thereafter, the processing circuitry 55 scans the subject by controlling the mechanical mechanism 7 based on the mechanical mechanism control information (step S508).

When it is determined at step S503 that the automatic generation mode is activated (positive determination at step S503), the processing circuitry 55 determines whether the value of each of the pieces of position information acquired by the plurality of means exceeds a threshold (step S509). When the value exceeds the threshold (positive determination at step S509), the processing circuitry 55 generates, for a position at which the threshold is exceeded, a scanning path based on position information acquired through linear interpolation or the position information acquired by a means for which the threshold is not exceeded (step S510).

When the value does not exceed the threshold (negative determination at step S509), the processing circuitry 55 generates a scanning path based on the position information acquired by a means for which predetermined priority is high (step S511). After step S510 or S511, the processing circuitry 55 proceeds to processing at step S507 and executes the processing.

As described above, according to the fifth embodiment, the processing circuitry 55 controls display 3 to display a scanning path. Thus, the ultrasound diagnostic apparatus according to the fifth embodiment allows scanning path selection by the operator.

According to the fifth embodiment, the input interface 4 receives an operation on the scanning path displayed on the display 3. The processing circuitry 55 determines a scanning path on which the ultrasound probe 4 is moved in accordance with the operation received by the input interface 4. Thus, the ultrasound diagnostic apparatus according to the fifth embodiment allows scanning path edition by the operator.

According to the fifth embodiment, the processing circuitry 55 generates a scanning path by selecting any one of the distance based on the image and the distance based on the reflected wave data for each position to which the ultrasound probe 2 is moved relative to the subject. In addition, according to the fifth embodiment, the processing circuitry 55 generates a scanning path by selecting any one of the distance measured by the distance sensor and the distance based on the reflected wave data for each position to which the ultrasound probe is moved relative to the subject. Thus, the ultrasound diagnostic apparatus according to the fifth embodiment allows scanning path generation at higher accuracy.

Sixth Embodiment

The first to fifth embodiments are described above, but various different kinds of forms other than the first to fifth embodiments described above are possible.

In the first to third embodiments described above, a scanning path separated from the body surface of the subject by a predetermined distance is generated. However, the embodiments are not limited thereto. For example, a scanning path on which the distance from the body surface is in a predetermined range may be generated. For example, a scanning path on which the distance from the body surface is "6 cm to 8 cm" may be generated.

In the above-described embodiments, the ultrasound probe 2 is connected with the apparatus main body 5 through a cable. However, the embodiments are not limited thereto. For example, ultrasonic wave transmission and reception by the ultrasound probe may be controlled in a wireless manner. In such a case, for example, the transmission-reception circuitry is built in the probe body of the ultrasound probe, and ultrasonic wave transmission and reception by the ultrasound probe are controlled from another apparatus in a wireless manner. The ultrasound diagnostic apparatus according to the present embodiment may include only such a wireless ultrasound probe.

In the above-described embodiments, the ultrasound diagnostic apparatus 1 executes various kinds of processing. However, the embodiment is not limited thereto. Part or all of the processing of scanning path generation executed by the ultrasound diagnostic apparatus 1 in the above description may be executed by the ultrasound scanning support apparatus. The ultrasound scanning support apparatus according to the present application may be achieved by a computer or the like or may be achieved by the mechanical mechanism 7. For example, when the ultrasound scanning support apparatus is achieved by the mechanical mechanism 7, part or all of the processing of scanning path generation executed by the ultrasound diagnostic apparatus 1 in the above description is executed by the mechanical mechanism 7 as the ultrasound scanning support apparatus.

The term "processor" used in the above description means, for example, a central processing unit (CPU), a graphics processing unit (CPU), or a circuit such as an application specific integrated circuit (ASIC) or a programmable logic device (for example, a simple programmable logic device (SPLD), a complex programmable logic device (CPLD), or a field programmable gate array (FPGA)). The processor achieves a function by reading and executing a computer program stored in a storage circuit. Instead of being stored in the storage circuit, the computer program may be directly incorporated in a circuit of the processor. In this case, the processor achieves the function by reading and executing the computer program incorporated in the circuit. Each processor according to the present embodiment is not limited to a configuration as a single circuit for the processor but may be configured as one processor obtained by combining a plurality of independent circuits to achieve the function thereof.

Each illustrated component of each device in the above-described embodiments is functionally conceptual and does not necessarily need to be physically configured as illustrated. Specifically, specific forms of distribution and integration of the devices are not limited to those illustrated, but all or part thereof may be functionally or physically distributed or integrated in optional units in accordance with various loads, use status, and the like. Moreover, all or optional part of the processing function performed by each device may be achieved by a CPU and a computer program analyzed and executed by the CPU or may be achieved as wired logic hardware.

Each processing method in the above-described embodiments may be achieved by executing a processing program prepared in advance through a computer such as a personal computer or a work station. The processing program may be distributed through a network such as the Internet. In addition, the processing program may be recorded in a computer-readable non-transitory recording medium such as a hard disk, a flexible disk (FD), a CD-ROM, an MO, a DVD, or a Flash memory such as a USB memory or an SD card memory, and may be read from the non-transitory recording medium and executed by a computer.

As described above, according to the embodiments, it is possible to easily generate a scanning path.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound automatic scanning system, comprising:
an ultrasound probe configured to transmit and receive an ultrasonic wave;
a mechanical mechanism including a motor configured to move the ultrasound probe while an ultrasonic-wave transmission-reception surface of the ultrasound probe is pointed to a subject; and
processing circuitry configured to
acquire a first distance between a body surface of the subject and the ultrasonic-wave transmission-reception surface of the ultrasound probe based on a first distance measurement method, and compare the first distance with a first threshold,
acquire a second distance between a body surface of the subject and the ultrasonic-wave transmission-reception surface of the ultrasound probe based on a second distance measurement method different from the first distance measurement method, and compare the second distance with a second threshold,
calculate, based on at least one of the first distance that is determined to be less than or equal to the first threshold and the second distance that is determined to be less than or equal to the second threshold, a coordinate of a position that is a predetermined distance from the body surface and between the body surface of the subject and the ultrasonic-wave transmission-reception surface of the ultrasound probe, for each position along a moving direction of the ultrasound probe, and
connect the calculated coordinates along the moving direction of the ultrasound probe to generate locus information of movement of the ultrasound probe when ultrasound scanning is executed on the subject,
wherein the mechanical mechanism is configured to execute ultrasound scanning on the subject by moving the ultrasound probe based on the locus information generated by the processing circuitry.

2. The ultrasound automatic scanning system according to claim 1, wherein the processing circuitry is further configured to:
acquire the first distance based on reflected wave data collected while the ultrasound probe is moved by the mechanical mechanism,
acquire the second distance based on an image obtained by capturing a state in which the ultrasound probe is moved relative to the subject in a non-contact manner by the mechanical mechanism, and
generate the locus information based on at least one of the first distance that is determined to be less than or equal to the first threshold and the second distance that is determined to be less than or equal to the second threshold.

3. The ultrasound automatic scanning system according to claim 2, wherein the processing circuitry is further configured to generate the locus information by selecting one of the second distance that is determined to be less than or equal to the second threshold based on the image and the first distance that is determined to be less than or equal to the first threshold based on the reflected wave data at each position along the moving direction to which the ultrasound probe is moved relative to the subject.

4. The ultrasound automatic scanning system according to claim 1, wherein the processing circuitry is further configured to:
acquire the first distance based on reflected wave data collected while the ultrasound probe is moved by the mechanical mechanism,
acquire the second distance based on distance information acquired by a distance meter while the ultrasound probe is moved relative to the subject in a non-contact manner by the mechanical mechanism, and
generate the locus information based on at least one of the first distance that is determined to be less than or equal to the first threshold and the second distance that is determined to be less than or equal to the second threshold.

5. The ultrasound automatic scanning system according to claim 4, wherein the processing circuitry is further configured to generate the locus information by selecting one of the second distance that is determined to be less than or equal to the second threshold based on the distance information measured by the distance meter and the first distance that is determined to be less than or equal to the first threshold based on the reflected wave data at each position along the moving direction to which the ultrasound probe is moved relative to the subject.

6. The ultrasound automatic scanning system according to claim 1, wherein the processing circuitry is further configured to:
calculate a distance by which the ultrasound probe is to be separated from the body surface of the subject based on a focal point of the ultrasound probe, and
generate the locus information based on the calculated distance and at least one of the first distance that is determined to be less than or equal to the first threshold and the second distance that is determined to be less than or equal to the second threshold.

7. The ultrasound automatic scanning system according to claim 1, wherein the processing circuitry is further configured to generate the locus information based on pressure applied between the subject and the ultrasound probe while the ultrasound probe is moved relative to the subject in a contact manner by the mechanical mechanism.

8. The ultrasound automatic scanning system according to claim 1, wherein the processing circuitry is further configured to generate, based on information of a three-dimensional positional relation between the ultrasound probe moved by the mechanical mechanism and the subject, angle information of the ultrasound probe when the ultrasound scanning is executed on the subject.

9. The ultrasound automatic scanning system according to claim 1, wherein the ultrasound scanning is executed on the subject while an acoustic medium is provided between the ultrasound probe and the subject, and the ultrasound probe is not in contact with the body surface of the subject.

10. The ultrasound automatic scanning system according to claim 1, wherein the processing circuitry is further configured to cause a display to display the locus information.

11. The ultrasound automatic scanning system according to claim 10, further comprising an input interface configured to receive an operation on the locus information displayed on the display, wherein the processing circuitry is further configured to determine, in accordance with the operation received by the input interface, the locus information based on which the ultrasound probe is moved.

12. The ultrasound automatic scanning system of claim 1, wherein the first distance measurement method is provisional scanning using the ultrasound probe and the second distance measurement method includes capturing an image with an optical camera.

13. An ultrasound diagnostic apparatus comprising:
an ultrasound probe configured to transmit and receive an ultrasonic wave, and moved by a mechanical mechanism including a motor configured to move the ultrasound probe while an ultrasonic-wave transmission-reception surface of the ultrasound probe is pointed to a subject; and
processing circuitry configured to
acquire a first distance between a body surface of the subject and an ultrasonic-wave transmission-reception surface of the ultrasound probe based on a first distance measurement method, and compare the first distance with a first threshold,
acquire a second distance between a body surface of the subject and the ultrasonic-wave transmission-reception surface of the ultrasound probe based on a second distance measurement method different from the first distance measurement method, and compare the second distance with a second threshold,
calculate, based on the at least one of first distance that is determined to be less than or equal to the first threshold and the second distance that is determined to be less than or equal to the second threshold, a coordinate of a position that is a predetermined distance from the body surface and between the body surface of the subject and the ultrasonic-wave transmission-reception surface of the ultrasound probe, for each position along a moving direction of the ultrasound probe, and
connect the calculated coordinates along the moving direction of the ultrasound probe to generate locus information of movement of the ultrasound probe when ultrasound scanning is executed on the subject,
wherein the mechanical mechanism is configured to execute ultrasound scanning on the subject by moving the ultrasound probe based on the locus information generated by the processing circuitry.

14. An ultrasound scanning support apparatus, comprising:
processing circuitry configured to
acquire a first distance between a body surface of a subject and an ultrasonic-wave transmission-reception surface of an ultrasound probe configured to transmit and receive an ultrasonic wave based on a first distance measurement method, and compare the first distance with a first threshold, the ultrasound probe being moved by a mechanical mechanism including a motor configured to move the ultrasound probe while the ultrasonic-wave transmission-reception surface of the ultrasound probe is pointed to the subject,
acquire a second distance between a body surface of the subject and the ultrasonic-wave transmission-reception surface of the ultrasound probe based on a second distance measurement method different from the first distance measurement method, and compare the second distance with a second threshold,
calculate, based on at least one of the first distance that is determined to be less than or equal to the first threshold and the second distance that is determined to be less than or equal to the second threshold, a coordinate of a position that is a predetermined distance from the body surface and between the body surface of the subject and the ultrasonic-wave transmission-reception surface of the ultrasound probe, for each position along a moving direction of the ultrasound probe, and
connect the calculated coordinates along the moving direction of the ultrasound probe to generate locus information of movement of the ultrasound probe when ultrasound scanning is executed on the subject.

15. The ultrasound scanning support apparatus according to claim 14, further comprising the mechanical mechanism.

* * * * *